US 6,587,845 B1

(12) United States Patent
Braunheim

(10) Patent No.: US 6,587,845 B1
(45) Date of Patent: Jul. 1, 2003

(54) METHOD AND APPARATUS FOR IDENTIFICATION AND OPTIMIZATION OF BIOACTIVE COMPOUNDS USING A NEURAL NETWORK

(75) Inventor: Benjamin B. Braunheim, 18 E. 105th St., Apt. 12, New York, NY (US) 10029

(73) Assignee: Benjamin B. Braunheim, New York, NY (US)

( * ) Notice: Subject to any disclaimer, the term of this patent is extended or adjusted under 35 U.S.C. 154(b) by 0 days.

(21) Appl. No.: 09/504,407

(22) Filed: Feb. 15, 2000

(51) Int. Cl.[7] .......................... G06F 15/18; G06G 7/00
(52) U.S. Cl. ............................................ 706/21; 706/20
(58) Field of Search ............................. 706/20, 21

(56) References Cited

U.S. PATENT DOCUMENTS

| | | | | |
|---|---|---|---|---|
| 4,461,619 A | * | 7/1984 | Hendry et al. | 434/295 |
| 5,214,715 A | * | 5/1993 | Carpenter et al. | 706/20 |
| 5,631,469 A | * | 5/1997 | Carrieri et al. | 250/341.5 |
| 5,727,128 A | * | 3/1998 | Morrison | 706/45 |
| 5,825,645 A | * | 10/1998 | Konar et al. | 706/20 |
| 5,933,819 A | * | 8/1999 | Skolnick et al. | 706/21 |
| 6,119,111 A | * | 9/2000 | Gross et al. | 706/15 |
| 6,185,548 B1 | * | 2/2001 | Schwartz et al. | 706/21 |
| 6,289,328 B2 | * | 9/2001 | Shaffer | 706/20 |
| 6,295,514 B1 | * | 9/2001 | Agrafiotis et al. | 703/12 |
| 6,314,414 B1 | * | 11/2001 | Keeler et al. | 706/21 |

OTHER PUBLICATIONS

Su et al.; "Neural Model Predictive Control of Nonlinear Chemical Processes". Proceedings of the 1993 IEEE International Symposium on Intelligent Control, Aug. 1993, p. 358–363.*

Lambert et al.; "Application of Feedforward and Recurrent Neural Networks to Chemical Plant Predictive Modeling". IJCNN–91–Seattle International Joint Conference on Neural Networks, Jul. 1991, vol. 1, p. 373–378.*

Rivas et al.; "Dynamic Modelling Using a Multiple Neural Network Architecture". International Conference on Control, Mar. 1994, vol. 2, p. 977–982.*

Barton et al.; "Online Prediction of Polymer Product Quality in an Industrial Reactor Using Recurrent Neural Networks". International Conference on Neural Networks, Jun. 1997, vol. 1, p. 111–114.*

Roberts et al.; "Training Neural Networks to Identify Coding Regions in Genomic DNA". Fourth International Conference on Artificial Neural Networks, Jun. 1995, p. 399–403.*

Zhang et al.; "Protein Structure Prediction by a Data–Level Parallel Algorithm". Proceedings of the 1989 Conference on Supercomputing, Aug. 1989, p. 215–223.*

* cited by examiner

Primary Examiner—Emanuel Todd Voeltz
Assistant Examiner—Kelvin Booker
(74) Attorney, Agent, or Firm—Bradley M. Ganz, Esq.; Ganz Law, PC

(57) ABSTRACT

A computational method for the discovery and design of therapeutically valuable bioactive compounds is presented. The method employed has successfully analyzed enzymatic inhibitors for their chemical properties through the use of a neural network and associated algorithms. This method is an improvement over the current methods of drug discovery which often employs a random search through a large library of synthesized chemical compounds or biological samples for bioactivity related to a specific therapeutic use. This time-consuming process is the most expensive portion of current drug discovery methods. The development of computational methods for the prediction of specific molecular activity will facilitate the design of novel chemotherapeutics or other chemically useful compounds. The novel neural network provided in the current invention is "trained" with the bioactivity of known compounds and then used to predict the bioactivity of unknown compounds.

59 Claims, 13 Drawing Sheets

(7 of 13 Drawing Sheet(s) Filed in Color)

Double Neural Network

Neural Network

Double Neural Network

Geometry Comparisons of Unaltered Input Molecules and Ideal Molecules

Input molecule 4 ■ compared to input molecule 2

Input molecule 4 ■ compared to ideal molecule 4

Input molecule 2 ■ compared to ideal molecule 2

Molecules of Interest in Exemplary Study

Molecules of Interest in Exemplary Study

Molecules of Interest in Exemplary Study

Molecules of Interest in Exemplary Study

Comparison of Unaltered Input
Molecule 4 and Ideal Molecule 4

Unaltered input molecule 4

Ideal molecule 4

Comparison of Unaltered Input Molecule 9 and Ideal Molecule 9

Unaltered input molecule 9

Ideal molecule 9

Comparison of Unaltered Input Molecule 14 and Ideal Molecule 14

Unaltered input molecule 14

Ideal molecule 14

Comparison of Unaltered Input Molecule 1 and Ideal Molecule 1

Unaltered input molecule 1

Ideal molecule 1

Comparison of Unaltered Input Molecule 12 and Ideal Molecule 12

Unaltered input molecule 12

Ideal molecule 12

Comparison of Unaltered Input Molecule 15 and Ideal Molecule 15

Unaltered input molecule 15

Ideal molecule 15

METHOD AND APPARATUS FOR IDENTIFICATION AND OPTIMIZATION OF BIOACTIVE COMPOUNDS USING A NEURAL NETWORK

FIELD OF THE INVENTION

The invention pertains to the field of using computational methods in predictive chemistry. More particularly, the invention utilizes a neural network with associated algorithmic functions, and the quantum mechanical properties of the molecules investigated or portions of those molecules, to optimize the prediction of bioactivity or the mode of chemotherapeutic action for molecules of interest.

BACKGROUND OF THE INVENTION

The role of medicinal chemist has not been altered in several decades. Their efforts to identify chemotherapeutic compounds, and thereafter devise more potent variations to them for medicinal use has long been one involving the arduous task of testing one compound at a time to determine individual bioactivity. This slow throughput system is made even more costly by the fact that historically over 10,000 compounds must be individually tested and evaluated for every one that actually reaches market as a therapeutic agent, as discussed in SCRIP, World Pharmaceutical News, Jan. 9, 1996, (PJB Publications). These facts have driven many scientists and pharmaceutical houses to shift their research from traditional drug discovery (e.g. individual evaluation) towards the development of high throughput systems (HTP) or computational methods that will bring to bear increasingly powerfull computer technology for the drug discovery process. To date none of these systems have been proven to significantly shorten discovery and optimization time for the development of chemotherapeutic agents.

The first attempts to develop computational methods to predict the inhibitory potency of a given molecule prior to synthesis have been broadly termed quantitative structure activity relationship (QSAR) studies. These techniques require the user to define a functional relationship between a specific molecular property and a given molecular action. In the QSAR approach, or any approach where an individual is responsible for adjusting a mathematical model, the investigator must use variations in the structure of a molecule as the motivation for changing the value of coefficients in the computer model. For a chemical reaction as complex as an enzymatically mediated transformation of reactants to product, often an important part of therapeutic or medicinal activity, it is not possible to predict a priori all the effects a change to a substrate molecule will have on enzymatic action. This fact has made the QSAR approach to drug discovery exceptionally impracticable and inefficient.

Accordingly, a need exists to optimize the prediction of bioactivity in chemical compounds such that the discovery and development of therapeutically valuable compounds is made more rapid and efficient.

SUMMARY OF THE INVENTION

Briefly stated, the invention described herein provides a neural network approach to the prediction of chemical activity in at least one molecule of interest. The example provided herein demonstrates how this methodology is useful in the prediction of bioactivity for a molecule capable of acting as an enzymatic inhibitor. This same methodology is also applicable to a variety of compounds of interest using the same training protocols and the same quantum mechanical properties of given molecules, or portions thereof discussed herein.

The neural network provided herein is comprised of an input layer having at least one neuron where input data is sent and then given a vector value, a hidden layer having at least one neuron such that when data is received from the input layer that vector data is multiplied by a set weight and thereafter generates a weight matrix having the dimensions n by m where n is the length of an input vector and m is the number of hidden layer neurons available, and an output layer consisting of at least one neuron where the weight matrix data is sent before it is then sent to a transfer function. The transfer function is a non-linear equation that is capable of taking any value generated by the output layer and returning a number between −1 and 1.

Feed-forward neural networks with back-propagation of error, of the type disclosed herein (see pages 7–10), are trained to recognize the quantum mechanical electrostatic potential and geometry at the entire van der Waals surface of a group of training molecules and to predict the strength of interactions, or free energy of binding, between an enzyme and novel inhibitors of that enzyme. More generally, the input for the functions of the neural network are the quantum mechanical electrostatic potentials of various molecules of interest. The predictive value of the system is gained through the use of a "training" process for the neural network using the known physicochemical properties of at least one training molecule, such as Inosine-Uridine Preferring Nucleoside Hydrolase (IU-NH). IU-NH is a nucleoside hydrolase from first isolated from the organism *Crithidia fasciculata*. The neural network is given input generated from the known electrostatic potential surfaces of the known molecules and attempts to predict the free energy of binding for that training set of molecules. When the neural network is able to accurately predict the free energy of binding of the training set of molecules, then the same neural network can be used with high accuracy to determine the free energy of binding, and hence the chemical characteristics, of unknown molecules.

Among the novel aspects of the present invention is the utilization in the current invention of the quantum mechanical electrostatic potential of the molecule of interest at the van der Waals surface of that molecule as the physicochemical descriptor. The entire surface for each molecule, represented by a discrete collection of points, serves as the input to the neural network. In this way the invention utilizes quantum mechanical means to describe the molecular activity of a compound of interest. With improved knowledge of molecular activity the method described herein provides for enhancing the predictive value of neural networks with regard to phyisicochemical properties of compounds of interest either with regard to therapeutic compounds or compounds that would have other commercial or scientific value. The neural networks provided herein are useful in modeling chemical interactions that are non-covalent in nature. That is, as long as a reaction is mediated by electrostatic forces, including Van der Waals forces, the neural networks provided herein, and the associated algorithms, are accurate predictors of chemical activity and interaction. In this way they will save time and money in drug discovery and chemical evaluation processes. Specifically, with regard to enzymatic action, the neural networks herein described are able to determine chemical configurations that will optimize known chemotherapeutics and allow the discovery of new compounds that need to have specific binding characteristics or activity. These new compounds can be developed by modeling the quantum characteristics of specific molecular moieties with a trained neural or double neural network.

According to an exemplary embodiment of the invention, a computational method has been developed to predict the free energy of binding for inhibitor or untested enzyme molecules.

Other features and advantages of this invention will become apparent in the following detailed description of a preferred embodiment of this invention with reference to the accompanying drawings.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DESCRIPTION OF THE PREFERRED EMBODIMENT

Figure 1:
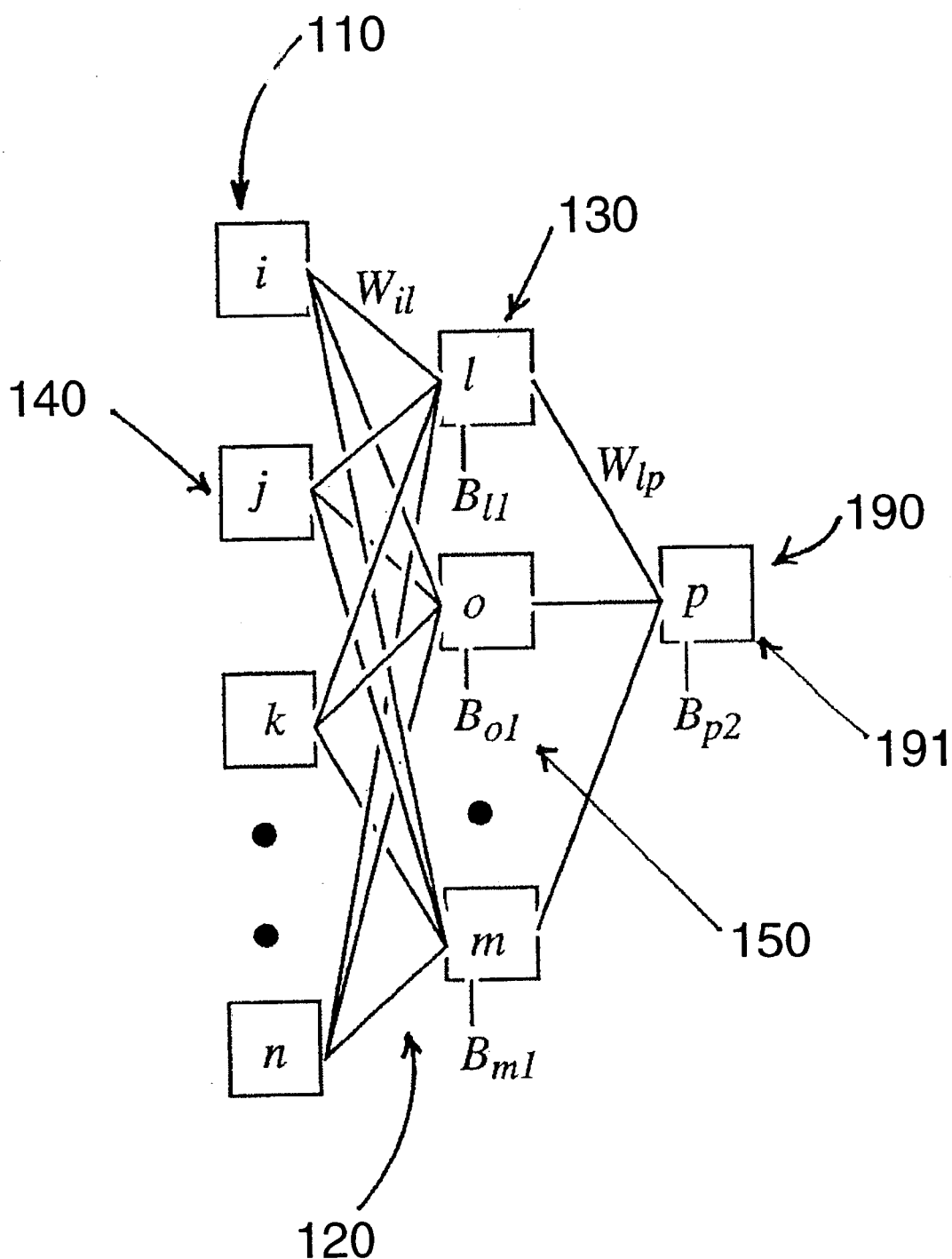
FIG. 1 shows a neural network with a back-propagation of error function, with an input layer i through n, a hidden layer j through m, and output layer p. The biases B are added to the hidden and output layers.

The following abbreviations have designated meanings in the specification:
Abbreviation Key
  High Throughput System: (HTP)
  Inosine-Uridine Preferring Nucleoside Hydrolase: (IU-NH)
  Quantitative Structure Activity Relationship (QSAR)
  p-aminophenyliminoribitol (pAPIR)
Neural Networks The present invention discloses a neural network for improving the identification of chemically useful compounds without having to test each investigated compound individually. As is known in the art, a computational neural network is a computer algorithm which, during its training process, can learn features of input patterns and associate these with an output. Neural networks learn to approximate the function defined by the input/output pairs. The function is rarely, if ever specified by the user. After the learning phase, a well-trained network should be able to predict an output for a pattern not in the training set. In the context of the present invention, the neural net is trained with a set of molecules which can act as inhibitors for a given enzyme until the neural network can associate with every quantum mechanical description of the molecules in this set, a free energy of binding (which is the output). The network is then used to predict the free energy of binding for unknown molecules.

Known computational neural networks are composed of many simple units operating in parallel. These units and the aspects of their interaction are inspired by biological nervous systems. The network's function is largely determined by the interactions between units. An artificial neural network consists of a number of "neurons" or "hidden units" that receive data from the outside, process the data, and output a signal. A "neuron" is essentially a regression equation with a non-linear output. When more than one neuron is used, non-linear models can be fitted.

Networks learn by adjusting the values of the connections between elements (Fausett, L. FUNDAMENTALS OF THE NEURAL NETWORKS; Prentice Hall: New Jersey, 1994). The neural network presented by this invention is a feed-forward model with the back-propagation of error. This type of art recognized neural network learns with momentum. A back propagation neural network has three layers: an input layer, a hidden layer, and an output layer. The input layer is where the input data is sent. The link between the layers of the network is one of multiplication by a weight matrix, where every entry in the input vector is multiplied by a weight and sent to every hidden layer neuron, so that the hidden layer weight matrix has the dimensions n by m, where n is the length of the input vector and m is the number of hidden layer neurons. A bias is added to the hidden and output layer neurons. The hidden layer then functions to scale all the arguments before they are input into the transfer function. Each neuron has one bias. The function of the bias is to adjust the influence of neurons with greater and lesser roles in the model that the neural network is learning how to model.

Neural Network Formulas

Referring to the schematic in FIG. 1, the input layer 110 is represented by the boxes at the top-left of the figure. The weights 120 are represented by the lines connecting the layers: $w_{ij}$ is the weight between the $i^{th}$ neuron of the input layer and $j^{th}$ neuron of the hidden layer 130 and $w_{jk}$ is the weight between the $j^{th}$ neuron of the hidden layer 130 and the $k^{th}$ neuron of the output layer 190. In FIG. 1 the output layer 190 has, as an exemplary example, only one neuron 191 because the target pattern is a single number, the binding energy (represented as "$B_{p2}$"). The hidden layer 130 input from pattern number 1 for neuron 140 j, is $h'_j$, and is calculated:

$$h^1_j(1) = b_j + \sum_{i=1}^{n} x^o_i(1) \times w_{ij} \qquad \text{Formula[1]}$$

where $x^o_i$ is the output from the $i^{th}$ input neuron, $w_{ij}$ is the element of the weight matrix connecting input from neuron i with hidden layer neuron j and $b_j$ is the bias 150 on the hidden layer neuron j. This vector $h'_j$ is sent through a transfer function, $f$. This function is non-linear and usually sigmoidal, taking any value and returning a number between −1 and 1, see page 4, (Fausett, L. FUNDAMENTALS OF THE NEURAL NETWORKS; Prentice Hall: New Jersey, 1994). A typical example is:

$$f(h^1_j) = \frac{2}{1+e^{-h^1_j}} - 1 \equiv h^o_j \qquad \text{Formula[2]}$$

The hidden layer output, $h^o_j$ is then sent to the output layer 190. The output layer input $o^i_k$ is calculated for the $k^{th}$ output neuron $$o^1_k = b_k + \sum_{j=1}^{m} h^o_j w_{jk} \qquad \text{Formula[3]}$$

where $w_{jk}$ is the weight matrix element connecting hidden layer neuron j with output layer neuron k. The output layer output, $o^o_k$, is calculated with a similar transfer function as the one given above:

$$g(o^1_k) = \frac{\gamma}{1+e^{(-o^1_k)}} - \eta \equiv o^o_k \qquad \text{Formula[4]}$$

where $\gamma_i$ is the range of the binding energies of the molecules used in the study and $\eta_i$ is the minimum number of all the binding energies. The minimum and maximum values are decreased and increased 10% to give the neural network the ability to predict numbers larger and small than those in the training set:

$$\min_{new}=\min_{old}-abs(\min_{old}x.1), \qquad \text{Formula[5]}$$

$$\max_{new}=\max_{old}+abs(\max_{old}x.1) \qquad \text{Formula[6]}$$

The calculation of an output concludes the feed forward phase of training. The weights and biases are initialized with random numbers, during the first iterations the output of the network will be random numbers. Back propagation of error is used in conjunction with learning rules to increase the accuracy of predictions. The difference between $o^o_k$ and the target value for input pattern number 1, $t_k$, determines the sign of the corrections to the weights and biases. The size of the correction is determined by the first derivative of the transfer function. The relative change in weights and biases are proportional to a quantity $\delta_k$:

$$\delta_k=(t_k-o^o k)g'(o^1_k) \qquad \text{Formula[7]}$$

where g' is the first derivative of equation 4. The corrections to the weights and biases are calculated:

$$\Delta w_{jk}=\alpha\delta_k h^o_j \qquad \text{Formula[8]}$$

$$\Delta b_k=\alpha\delta_k \qquad \text{Formula[9]}$$

The corrections are moderated by $\alpha$, the learning rate, this number ranges from zero to one exclusive of the end points. $\alpha$ functions to prevent the network from training to be biased to the last pattern of the iteration. The network's error should preferably be minimized with respect to all the patterns in the training set. The same learning rule is applied to the hidden layer weight matrix and biases. In most adaptive systems, learning is facilitated with the introduction of noise. In neural networks this procedure is called learning with momentum. The correction to the weights of the output layer at iteration number $\tau$ is a function of the correction of the previous iteration, $\tau-1$, and $\mu$, the momentum constant;

$$\Delta w_{jk}(\tau)=\alpha\delta_k h^o_j+\mu\Delta w_{jk}(\tau-1) \qquad \text{Formula [10]}$$

$$\Delta b_k(\tau)=\alpha\delta_k+\mu\Delta b_k(\tau-1) \qquad \text{Formula [11]}$$

The same procedure is applied to the hidden layer weights and biases. The correction terms are added to the weights and biases concluding the back-propagation phase of the iteration. The network can train for hundreds to millions of iterations depending on the complexity of the function defined by the input/output pairs. This type of back-propagation is a generalization of the known Widrow-Hoff learning rule applied to multiple-layer networks and non-linear differentiable transfer functions (Rumelhart, D. E.; Hinton, G. E.; Williams, R., *J. Parallel Distributed Processing*, Vol. 1; MIT Press: Massachusetts, 1986).

Input vectors and the corresponding output vectors are used to train until the network can approximate a function. The strength of a back-propagation neural network is its ability to form internal representations through the use of a hidden layer of neurons. For example, the "exclusive or" problem demonstrates the ability of neural networks, with hidden layers, to form internal representations and to solve complex problems. Suppose four input patterns [(0,1) (0,0) (1,0) (1,1)] with output targets [1, 0, 1, 0], respectively are used. A perceptron or other single layer system would be unable to simulate the function described by these four input/output pairs. The only way to solve this problem is to learn that the two types of inputs work together to affect the output. In this case the least similar inputs cause the same output, and the more similar inputs have different outputs (Rumelhart, D. E.; Hinton, G. E.; Williams, R., *J. Parallel Distributed Processing*, Vol. 1; MIT Press: Massachusetts, 1986).

The ability required to solve the aforementioned exemplary problem is not unlike that required to find the best inhibitor when it does not share all the same quantum features of the transition state. It is this inherent ability of neural networks to solve complex puzzles that makes them well conditioned for the task of simulating biological molecular recognition for a variety of molecule families including hydrolases, proteases, polymerases, transcriptases, phosphatases, and kinases. Each input neuron is given information (electrostatic potential or geometry) about the nearest point on the surface of the inhibitor. In this design each input neuron may be imagined to be at a fixed point on the sphere around the inhibitors, judging each inhibitor in the same way the enzyme active site would.

Training a neural network requires variation of four adjustable parameters; number of hidden layer neurons, the learning rate, momentum constant and number of training iterations. One way to tell that a network is well trained is to minimize the training set prediction error. This can be calculated by taking the difference between the target$_i$ value for a molecule (experimentally determined binding energy), and the number the neural network predicted for that pattern$_i$, and summing the absolute value of this number for all the molecules in the training set. As training progresses the training set prediction error will decrease. Minimizing training set error is not without negative consequence; over-training occurs when the network trains for too many iterations, has too many hidden layer neurons, has too large of a learning rate or too small of a momentum constant. One way to tell that a neural network has not been over-trained is to have it make a prediction for a pattern not in the training set. That is, see if the network can generalize from the information contained in the input/output pairs of the training set and apply that information to a molecule it has not trained with.

In accommodation of this fact a training set of molecules is used as an "adjuster" molecule. This molecule is left out of the training set during training and used to check if the neural network was over-trained. The procedure is to train the neural network until the prediction set error has decreased until it plateau's. At this point the training procedure is ended and the resulting neural network is tested with the previously unused adjuster molecule or molecules. Preferably, if the neural network predicts the adjuster molecules binding energy within 5%, that neural network's construction is saved, if the prediction is more than 5% off, a new construction is chosen. This procedure is repeated until a construction is found that allows the neural network to predict the adjuster molecule's binding energy within 5%. This is done for all of the molecules in the training set, and the most common neural network construction is chosen as the final construction. The final construction for this system is 5 hidden layer neurons, ten thousand iterations, learning rate equals 0.1 and the momentum term equals 0.9.

Quantum chemical data can also be input to train a neural network. As part of an exemplary description of a use of the present invention, quantum descriptions of molecules were created in the following way: First the molecular structures are energy minimized using semi-empirical methods. Molecules with many degrees of freedom, are configured such that they all have their flexible regions in the same relative position. Then the wave function for the molecule is calculated with an available software program Gaussian 94 (Gaussian 94, Revision C.2; Gaussian, Inc., Pittsburgh, Pa., 1995). Preferably, a variety of basis tests are used to insure converged results. From the wave function, the electrostatic potential is calculated at all points around and within the molecule. The electron density, the square of the wave function, is also calculated at all points around and within the molecule. With these two pieces of information the electrostatic potential at the van der Waals surface can be generated. Such information sheds light on the kinds of interactions a given molecule can have with the active site (Horenstein, B. A.; Schramm, V. L. Electronic nature of the transition state for nucleoside hydrolase—A blueprint for inhibitor design, *Biochemistry* 1993, 32, 7089–7097). Regions with electrostatic potentials close to zero are likely to be capable of van der Waals interactions, regions with a partial positive or negative charge can serve as hydrogen bond donor or acceptor sites, and regions with even greater positive or negative potentials may be involved in coulombic interactions.

The electrostatic potential also conveys information concerning the likelihood that a particular region can undergo electrophilic or nucleophilic attack. Since molecules described by quantum mechanics have a finite electron density in all space, a reasonable cutoff is required to define a molecular geometry. One choice is the van der Waals surface, within which 95% of the electron density is found. One can closely approximate the van der Waals surface by finding all points around a molecule where the electron density is close to 0.002 ±δ electrons/bohr (Wagener, M.; Sadowski, J.; Gasteiger, J., Autocorrelation of molecular surface properties for modeling corticasteriod binding globulin and cytosolic Ah receptor activity by neural networks, *J. Am. Chem. Soc.* 1995, 117, 7769–7775). In this formula δ is the acceptance tolerance, δ is adjusted so that about 15 points per atom are accepted, creating a fairly uniform molecular surface, as shown previously (Bagdassarian, C. K.; Braunheim, B. B.; Schramm, V. L.; Schwartz, S. D., Quantitative measures of molecular similarity: methods to analyze transition-state analogues for enzymatic reactions. *Int. J. Quantum Chem., Quant. Biol. Symp.* 1996, 23,73–80)(Hammond, D. J.; Gutteridge, W. E.; Purine and Pyrimidine Metabolism in the Trypanosomatide, *Molecular and Biochemical Parasitology*, 1984, 13, 243–261). The information about a given molecular surface is thus described by a matrix with dimensions of 4×n where n is the number of points for the molecule, and the row vector of length 4 contains the x,y and z-coordinates of a given point and the electrostatic potential at that point.

To preserve the geometric and electrostatic integrity of the training molecules, a collapse onto a lower dimensional surface is preferably avoided. The molecules are preferably oriented using common atoms and rotation matrices. Three atomic positions that all the molecules share are chosen and named a,b and c;–a is then translated to the origin, and this translation is performed on b and c and all the surface points. The basis set is rotated such that b is on the positive x axis. Then the basis set is rotated such that c is in the positive x, z plane. Inputs to a neural network must be in the form of a vector not a matrix. In an exemplary utilization of the present invention, the aforementioned transformation, the electrostatic potential of the different molecular surfaces was mapped onto a common surface; a sphere with a larger radius than the largest molecule in the study. The nearest neighbor for each point on the sphere is found on the surface of the molecule. The sphere is larger than the molecules so all mapping is outward. The electrostatic potential of this molecular point is then given the x, y and z coordinates of its nearest neighbor on the sphere. This mapping insures that similar parts of the molecules occupy a similar position in the input vector. The input to the neural network is a vector of these mapped electrostatic potentials and the distance the points were mapped from the molecular surface to the sphere. The information in the second half of the input vector are scalars that relate the distance, in Å (angstroms), between a point on the sphere and the nearest neighbor point on the molecule's surface. This portion of the input is designed to inform the neural network about the relative shapes and sizes of the molecular surfaces.

In the limit term of the algorithms, with an infinite number of points, all mappings are normal to the inhibitor's surface, and the mapping distances will be as small as possible. To approach this limit a ten fold excess of points was selected to describe the molecules. The molecule's surfaces are described by 150 points per atom.

The reference sphere that the points are mapped onto is described by a smaller number of points, 15 times the average number of atoms in the molecules of the study. As a result of mapping to the reference sphere all molecules are described by the smaller number of points.

Double Neural Networks

It is known in the art that neural networks can be used to predict how well molecules will function as inhibitors before experimental tests are done (Braunheim, B. B.; Schwartz, S. D. Computational Methods for Transition State and Inhibitor Recognition. Methods in Enzymology (In press); (Braunheim, B. B.; Schwartz, S. D.; Schramm, V. L. The Use of Quantum Neural Networks in a Blind Prediction of Unknown Binding Free Energies of Inhibitors to IU-Nucleoside Hydrolase, *J. Am. Chem. Soc.*, (Submitted)). The present invention, however, presents methods that can be used to design inhibitors that are more potent than those in the training set. Specifically, a double neural network has been devised whose function is to optimize the characteristics of molecules needed for bioactivity. A standard neural network, shown in FIG. 1, and whose function is determined by equations 1 through 10, is used to learn the rules of binding to the enzyme. Once a neural network has been trained to recognize what features of inhibitors are necessary to bind to the enzyme, this network is preferably integrated into another neural network to form a double neural network. The goal of this construction is to use these learned binding rules to discern how to create a quantum object which binds more strongly than any yet presented to the neural network.

Figure 2:
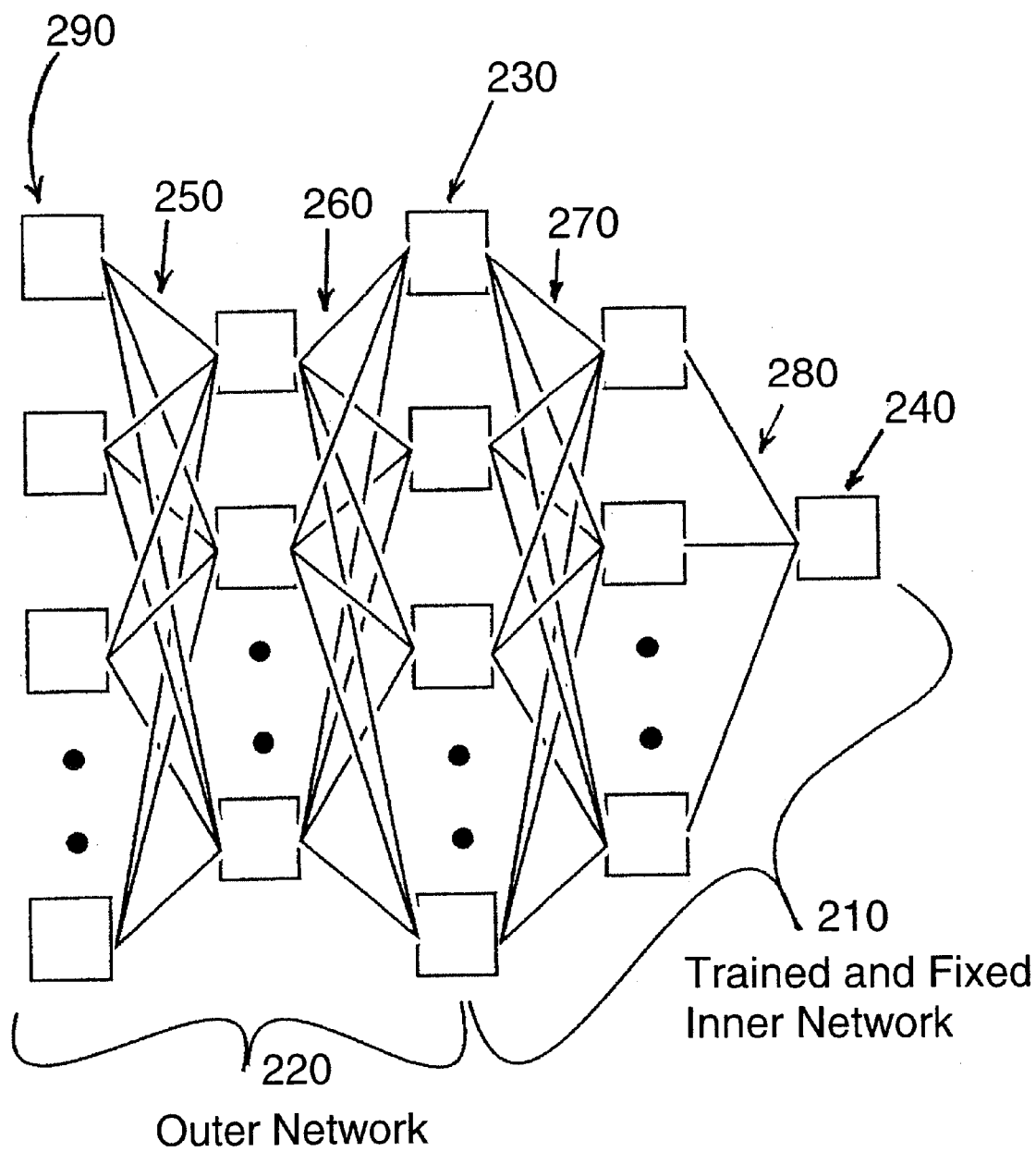
FIG. 2 shows a double neural network comprised of a coupled inner and outer neural network.

The trained and fixed network is called the inner network 210 and the other part is called the outer network 220, as seen in FIG. 2. The double network preferably has five layers and it is preferred that only the weights and biases between the first two layers 250 and 260, respectively, are allowed to vary during training. That is, during the training of the double network, the outer network's weights and biases, 250 and 260, respectively, are responsible for minimizing prediction set error. The inputs to the double network are preferably the same as the ones used to train the inner network, and input into first input layer 290. The outer network's output layer 230 is the input layer to the inner network, therefore the output of the outer network is the input to the inner network. The inner network's output values 240 are the same as those used before, the difference being that they have been decreased by least 1ΔG/RT. Preferably, they are decreased 3ΔG/RT. That is, they are the binding energies of slightly better inhibitors. To reduce the error of the inner network the outer network must output altered descriptions of the input molecule, but altered in a way such that it describes an inhibitor with a greater affinity for the enzyme. The outer network becomes an inhibitor "improver" because the inner network's fixed weights and biases contain the rules for binding to the enzyme. In order to compensate for the altered binding energies the outer network must output altered versions of the input molecules that would bind to the enzyme with greater affinity.

The inputs to the double neural network contain both electrostatic potential and geometrical information. During the training of the double neural network both of these descriptors are preferably allowed to vary. The range of the output functions of the output layer of the outer network 230 had to be modified in a similar way as that seen in formula 4 above, $$\delta_i(x) = (\gamma_i/1 + e^{(-x)}) - \eta_i \qquad \text{Formula [12]}$$

Where $\gamma_i$ is the range of the numbers at position i in the input patterns and $\eta_i$ is the minimum number at position i in the input patterns.

Preferably, the double neural network trains for many iterations in the same fashion as mentioned before, the only difference being that there is no established rule which defines the correct training parameters. When the inner network was trained the optimum number of hidden layer neurons, training iterations, learning rate and momentum term could be found through trial and error by testing if the network could make a prediction for a molecule not in the training set. The competency of the outer network cannot be tested independent of the inner network. This being the case the endpoint for training of the double network is preferably chosen as the minimum number of iterations and hidden layer neurons that were needed to minimize training error such that more iterations and hidden layer neurons did not decrease the error significantly. One skilled in the art will recognize that the preferable parameters discussed herein are matters of design choice, and can be varied based upon the preferences and experience of the user. The preferred construction for the double network was 5 hidden layer neurons (in the outer network) and 1 million training iterations. Preferably, the learning rate and momentum term were the same values used to train the inner network. After the double neural network is trained, improved versions of the molecular descriptions are output. These improved versions of input molecules are then transformed back into three dimensional representations of molecules. With the molecules in this format it is possible to identify the molecular features that the neural network found could be altered to result in improved binding characteristics, or in other desirable characteristics dependent upon the intent of the user. To test the double neural network concept, typically an enzyme with known binding or other characteristics is employed in the neural networks herein disclosed such that the molecule is optimized for improved chemical characteristics. The enzyme chosen was nucleoside hydrolase.

Use of Neural Networks in Biology

Neural networks have previously been used in the art in the task of simulating biological molecular recognition, Gasteiger et. al. have used Kohonen self-organizing networks to preserve the maximum topological information of a molecule when mapping its three-dimensional surface onto a plane (Gasteiger, J.; Li, X.; Rudolph, C.; Sadowski, J.; Zupan, J., Representation of molecular electrostatic potentials by topological feature maps. *J. Am. Chem. Soc.* 1994, 116, 4608–4620). Wagener et. al. have used auto-correlation vectors to describe different molecules. In that work (Wagener, M.; Sadowski, J.; Gasteiger, J. Autocorrelation of molecular surface properties for modeling corticasteriod binding globulin and cytosolic Ah receptor activity by neural networks. *J. Am. Chem. Soc.* 1995, 117, 7769–7775), the molecular electrostatic potential at the molecular surface was collapsed onto 12 auto-correlation coefficients.

Neural networks were used by Weinstein et. al., to predict the mode of action of different chemical compounds (Weinstein, J. N.; Kohn, K. W.; Grever, M. R.; Viswanadhan, V. N.; Rubinstein, L. V.; Monks, A. P.; Scudiero, D. A.; Welch, L.; Koutsoukos, A. D.; Chiausa, A. J.; Paull, K. D. Neural computing in cancer drug development: predicting mechanism of activity, *Science* 1992, 258, 447-451). The effectiveness of these chemical compounds on different malignant tissues served as one type of descriptor for future neural network methodologies. The predictive target for the neural network employed by Weinstein et al., was the mode of action of the chemical compounds tested (e.g. alkylating agent, topoisomerase I inhibitor, etc.). Tetko et. al., used a similar autocorrelation vectors approach (Tetko, I. V.; Tanchuk, V. Y.; Chentsova, N. P.; Antonenko, S. V.; Poda, G. I; Kukhar, V. P.; Luik, A. I. HIV- 1 reverse transcriptase inhibitor design using artificial neural networks. *J. Med. Chem.* 1994, 37, 2520–2526). So et al., used neural networks to learn and to predict biological activity from QSAR descriptions of molecular structure (Fausett, L. FUNDAMENTALS OF THE NEURAL NETWORKS; Prentice Hall: New Jersey, 1994). Neural networks were used by Thompson et. al. to predict the amino acid sequence that the HIV-1 protease would bind most tightly, and this information was used to design HIV protease inhibitors (Thompson, T. B.; Chou, K. -C.; Zheng, C. Neural network predictions of the HIV-1 protease cleavage sites. *J. Theor Biol.*, 1995, 177, 369–379).

As is known in the art, Neural networks are multidimensional non-linear function approximators. However, neural networks can also be used as a decision making algorithm because they require no assumptions about the function they are learning to approximate. This aspect of neural networks is important because it has been assumed in the prior art that the interactions between a chemical or enzymatic inhibitor and the active site of the molecule inhibited are determined by many aspects of the inhibitor and it would be impossible for an individual to a priori predict them all. In this sense the Schrodinger equation creates a complex, nonlinear relationship between a fixed enzyme active site and variable enzymatic inhibitors.

However, as disclosed herein, this non-linear relation is what neural networks can be used to discover and in this way can be manipulated to simulate or predict biological activity. The neural network learns to approximate a function that is defined by the input/output pairs. In the current invention the input is preferably a quantum mechanical description of a molecule and the output is the binding energy of that molecule with the enzyme.

After the neural network is "trained" with the quantum features of an appropriate set of molecules, of known bioactivity, this network construct has then "learned" the rules relating quantum descriptions to chemical recognition for that type of compound. The current inventions presents the way in which a neural network and/or a double neural network can be created which uses these rules to generate features that optimize bioactivity. The next section of the specification provides a generalization of the neural network concept to the "double neural network" of the current invention in which one neural network is trained to recognize binding features and a second coupled network optimizes these features. The next section of the specification contains application of the concepts to a specific multi-substrate enzyme IU nucleoside hydrolase.

EXAMPLE 1

Nucleoside Hydrolase

Protozoan parasites lack de novo purine biosynthetic pathways, and rely on the ability to salvage nucleosides from the blood of their host for RNA and DNA synthesis (Hammond, D. J.; Gutteridge, W. E., Purine and Pyrimidine Metabolism in the trypanosomatide, *Molecular and Biochemical Parasitology*, 1984, 13, 243–261). The inosine-uridine preferring nucleoside hydrolase (IU-NH) from Crithidia fasciculata is unique and has not been found in mammals (Degano, M.; Almo, S. C.; Sacchettini, J. C.; Schramm V. L. Trypanosomal nucleoside hydrolase, a novel mechanism from the structure of a transition state complex, Biochemistry, 1998, May). This enzyme catalyzes the N-ribosyl hydrolysis of all naturally occurring RNA purines and pyrimidines (Degano, M.; Almo, S. C.; Sacchettini, J. C.; Schramm V. L. Trypanosomal nucleoside hydrolase, a novel mechanism from the structure of a transition state complex, Biochemistry, 1998, May). The active site of the enzyme has two binding regions, one region binds ribose and the other binds the base. The inosine transition state requires $\Delta\Delta G=17.7$ kcal/mol activation energy, 13.1 kcals/mol are used in activation of the ribosyl group, and only 4.6 kcals/mol are used for activation of the hypoxanthine leaving group (Parkin, D. W.; Limberg, G.; Tyler, P. C.; Fumeau, R. H.; Chen, X. Y.; Schramm,V. L. Isozyme—specific transition state inhibitors for the trypanosomal nucleoside hydrolase. *Biochemistry*, 1997, 36(12), 3528–3419). Analogues that resemble the inosine transition state both geometrically and electronically have proven to be powerful competitive inhibitors of this enzyme and could be used as anti-trypanosomal drugs (Degano, M.; Almo, S. C.; Sacchettini, J. C.; Schramm V. L. Trypanosomal nucleoside hydrolase, a novel mechanism from the structure of a transition state complex Biochemistry, 1998, May).

The transition state for these reactions feature an oxocarbenium-ion achieved by the polarization of the C4' oxygen C1' carbon bond of ribose. The C4' oxygen is in proximity to a negatively charged carboxyl group from Glutamate 166 during transition state stabilization (Degano, M.; Almo, S. C.; Sacchettini, J. C.; Schramm V. L. Trypanosomal nucleoside hydrolase, a novel mechanism from the structure of a transition state complex Biochemistry, 1998, May). This creates a partial double bond between the C4' oxygen and the C1' carbon causing the oxygen to have a partial positive charge and the carbon to have a partial negative charge. Nucleoside analogues with iminoribitol groups have a secondary amine in place of the C4' oxygen of ribose and have proven to be effective inhibitors of IU-NH.

IU-NH acts on all naturally occurring nucleosides (with C2' hydroxyl groups), the lack of specificity for the leaving groups results from the small number of amino acids in this region to form specific interactions; Tyrosine 229, Histidine 82 and Histidine 241 (Degano, M.; Almo, S. C.; Sacchettini, J. C.; Schramm V. L. Trypanosomal nucleoside hydrolase, a novel mechanism from the structure of a transition state complex Biochemistry, 1998, May). The only crystal structure data available concerning the configuration of bound inhibitors was generated from a study of the enzyme bound to p-aminophenyliminoribitol (pAPIR). As seen in FIGS. 7a–7d, the Tyrosine 229 relocates during binding and moves above the phenyl ring of pAPIR. The side chain hydroxyl group of Tyrosine 229 is directed toward the cavity that would contain the six member ring of a purine, were it bound (Degano, M.; Almo, S. C.; Sacchettini, J. C.; Schramm V. L. Trypanosomal nucleoside hydrolase, a novel mechanism from the structure of a transition state complex Biochemistry, 1998, May). Histidine 82 is 3.6 Å(angstroms) from the phenyl ring of pAPIR, and in the proper position for positive charge-π interactions to occur (Degano, M.; Almo, S. C.; Sacchettini, J. C.; Schramm V. L. Trypanosomal nucleoside hydrolase, a novel mechanism from the structure of a transition state complex Biochemistry, 1998, May). Histidine 241 has been shown to be involved in leaving-group activation in the hydrolysis of inosine, presumably as the proton donor in the creation of hypoxanthine (Degano, M.; Almo, S. C.; Sacchettini, J. C.; Schramm V. L. Trypanosomal nucleoside hydrolase, a novel mechanism from the structure of a transition state complex Biochemistry, 1998, May).

The molecules used in the study are fixed such that their structures are consistent for all molecules. In the experiments it was assumed that the enzyme will bind all molecules in a similar low energy conformation. In the present invention this approach has been developed through experimentation on flexible linear chain inhibitors such as the arginine analogues for nitric oxide synthase. The double neural network of the current invention need not know the configuration as long as the conformation of all molecules that are presented to the neural network are consistent. The known crystal structure of the inhibitor p-aminophenyliminoribitol bound to IU-nucleoside hydrolase was used as the model chemical conformation.

The inosine transition state structure is stabilized by a negatively charged carboxyl group within the active site 3.6 Å from the C4' oxygen (Horenstein, B. A.; Parkin, D. W.; Estupinan, B.; Schramm, V. L. Transition-state analysis of nucleoside hydrolase from *Crithidia fasciculata*. *Biochemistry*, 1991, 30,10788–1079520). In order to simulate this aspect of the active site, a negatively charged fluoride ion (at the same relative position of the nearest oxygen of the carboxyl group) was included in the calculations of the electrostatic potential at the van der Waals surface.

To underscore the complexity of an investigation of this enzyme the different nature of transition state structures for the two different kinds of substrates was examined, purines and pyrimidines. Inosine's transition state is the only one for which there is a determined structure. The transition state structure for inosine is created by polarization of the ribosyl group across the C4' oxygen C1' bond, and protonation of N7 of the purine group. This protonation would be impossible when dealing with the pyrimidine uridine, as there is no place for this group to receive a proton (the electrons of N3 are involved in the ring conjugation). Therefore it is clear that these two types of substrates have quite different transition state structures, and that the rules of tight binding pyrimidine analogues is quite different from those of binding purines. For pyrimidines analogues, the binding energy tends to decrease with increasingly electron withdrawing substitutions. The opposite trend is seen with purine analogues. Any mathematical model of the binding preferences of this enzyme would have to take into account these contradictory trends with the different kinds of substrates. The prior art has determined that with this enzyme system a neural network could make accurate predictions for both purine and pyrimidine analogues when trained with purine and pyrimidine analogues (Braunheim, B. B.; Schwartz, S. D. Computational Methods for Transition State and Inhibitor Recognition. *Methods in Enzymology*. In press); (Braunheim, B. B.; Schwartz, S. D.; Schramm, V. L. The Use of Quantum Neural Networks in a Blind Prediction of Unknown Binding Free Energies of Inhibitors to IU-Nucleoside Hydrolase. *J. Am. Chem. Soc.* Submitted).

However, with the double neural network of the current invention, there is an added level of complexity, because the inner neural network must teach the outer network during training. That is, when the outer neural network improves the molecular descriptions, it is necessary for purines to be improved in different way than pyrimidines. However, with the use of the double neural network, predictions concerning bioactivity are significantly more precise and effective than previously seen in the art.

Surface Analysis of Tested Molecules

Because chemical reactivity is controlled by quantum mechanical properties, it was determined that a method could be developed to train neural networks with ab initio quantum chemical data. This method of the current invention has proven itself to be highly accurate in the prediction of binding strengths of diverse inhibitors to a variety of enzymatic systems. The current invention describes a new methodology which optimizes these quantum features to predict and then produce substances of therapeutic value, or commercial value, either through the development of de novo compounds or by providing a molecular structure useful in the search of existing chemical databases.

Figure 3A:
FIG. 3a shows surface point comparisons of the geometry of unaltered input molecules 4 and 2.
Figure 3B:
FIG. 3b shows surface point comparisons of the geometry of unaltered input molecule 4 and an idealized molecule 4.
Figure 3C:
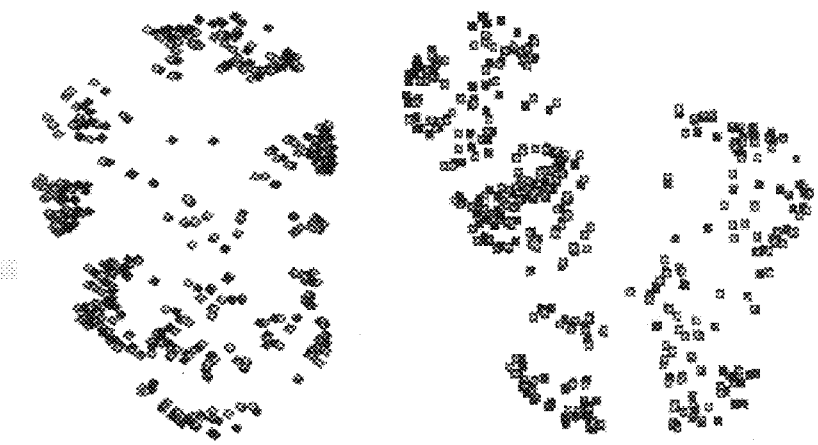
FIG. 3c shows surface point comparisons of the geometry of unaltered input molecule 2 and idealized molecule 2.
Figure 4:
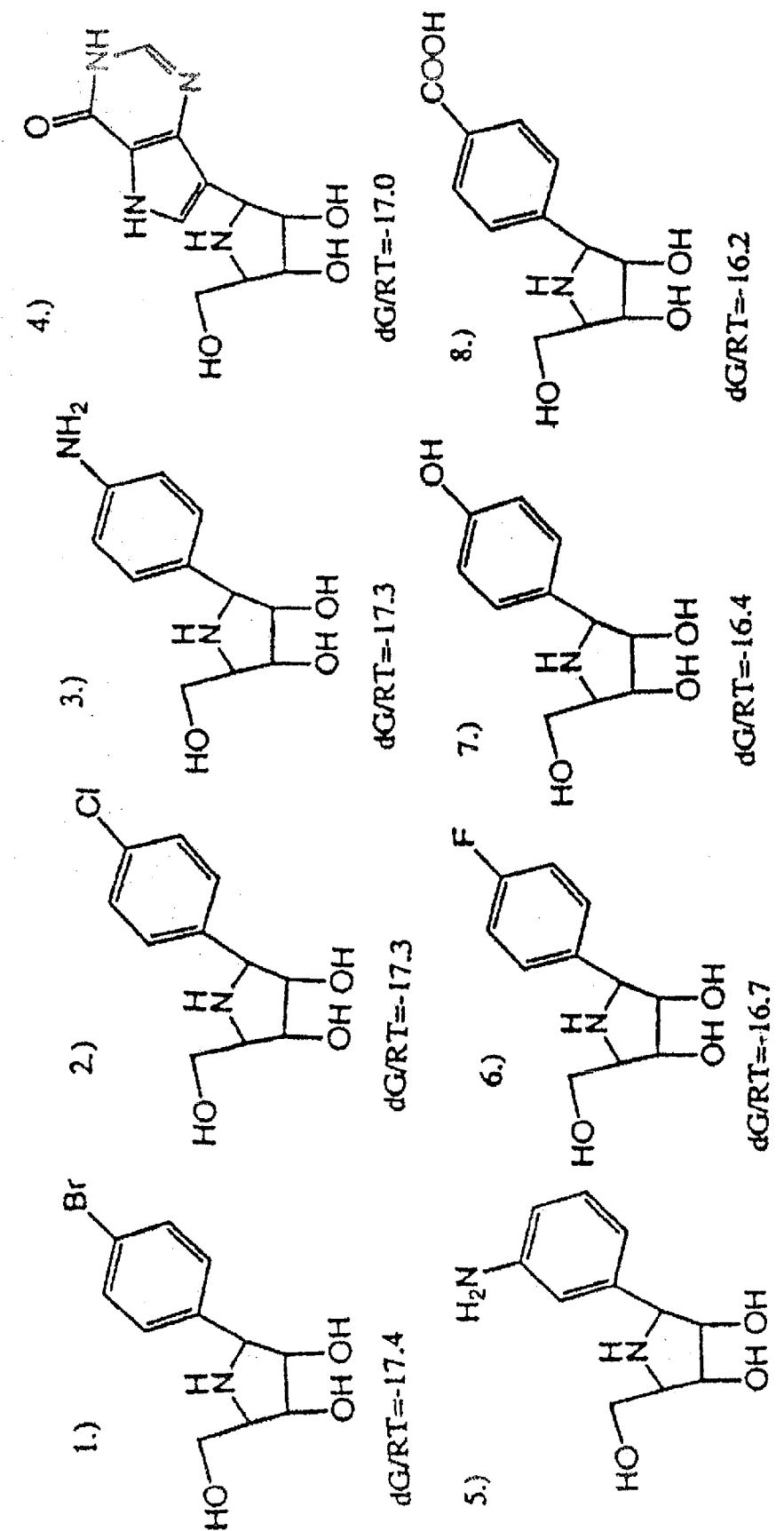
FIG. 4 shows a two dimensional representations of the molecules used in an exemplary study described herein.
Figure 4:
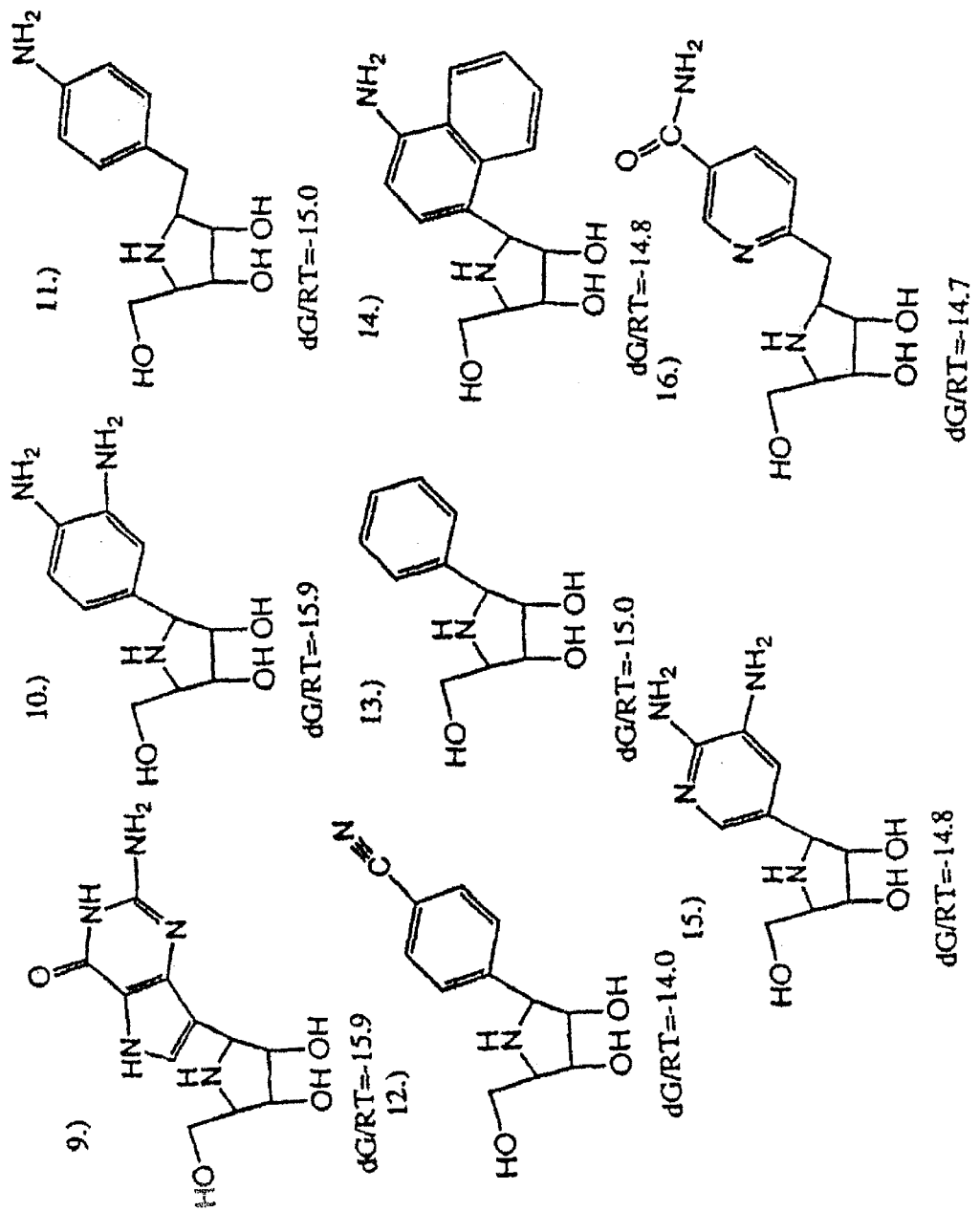
Figure 4:
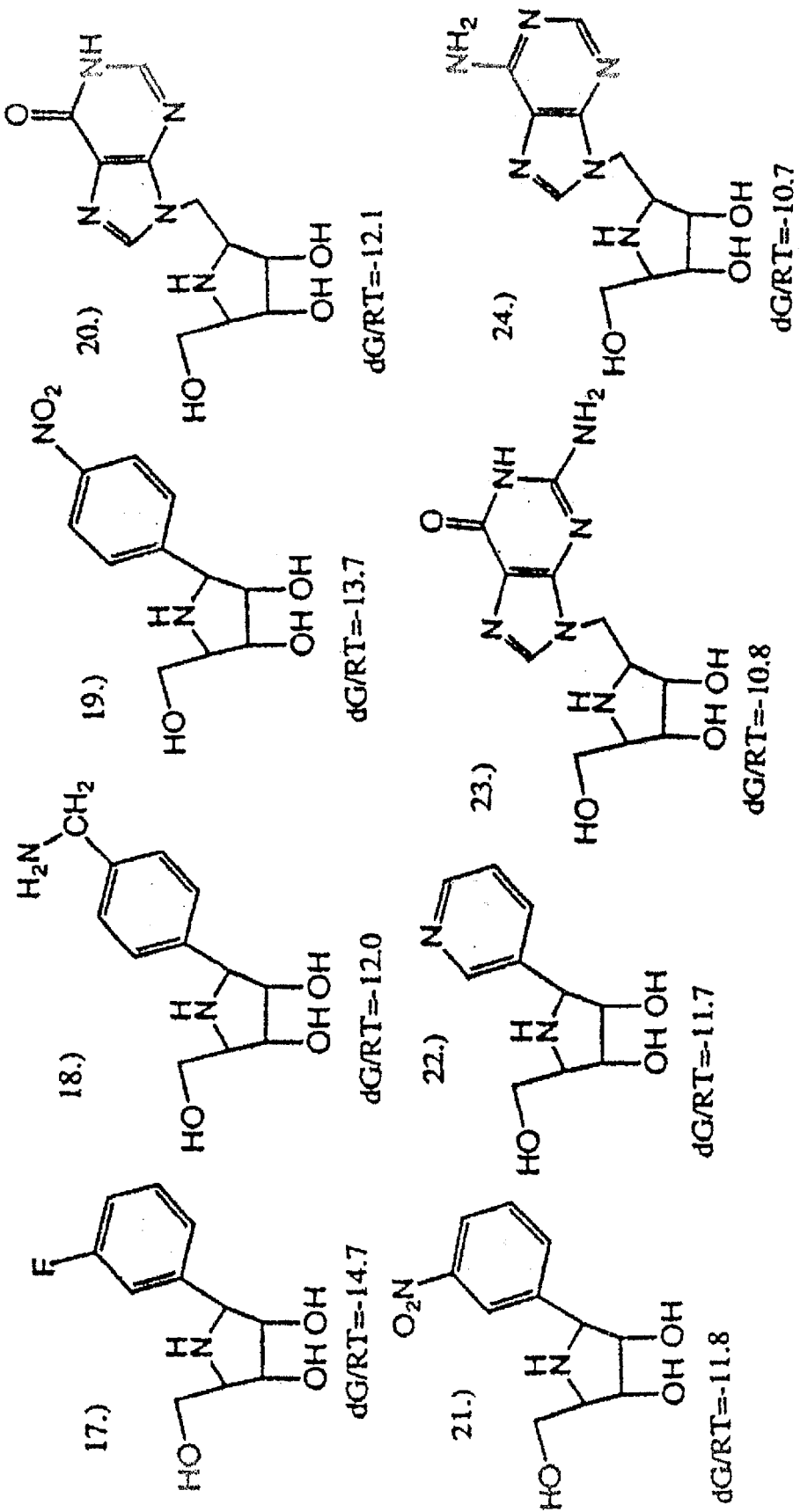
Figure 4:
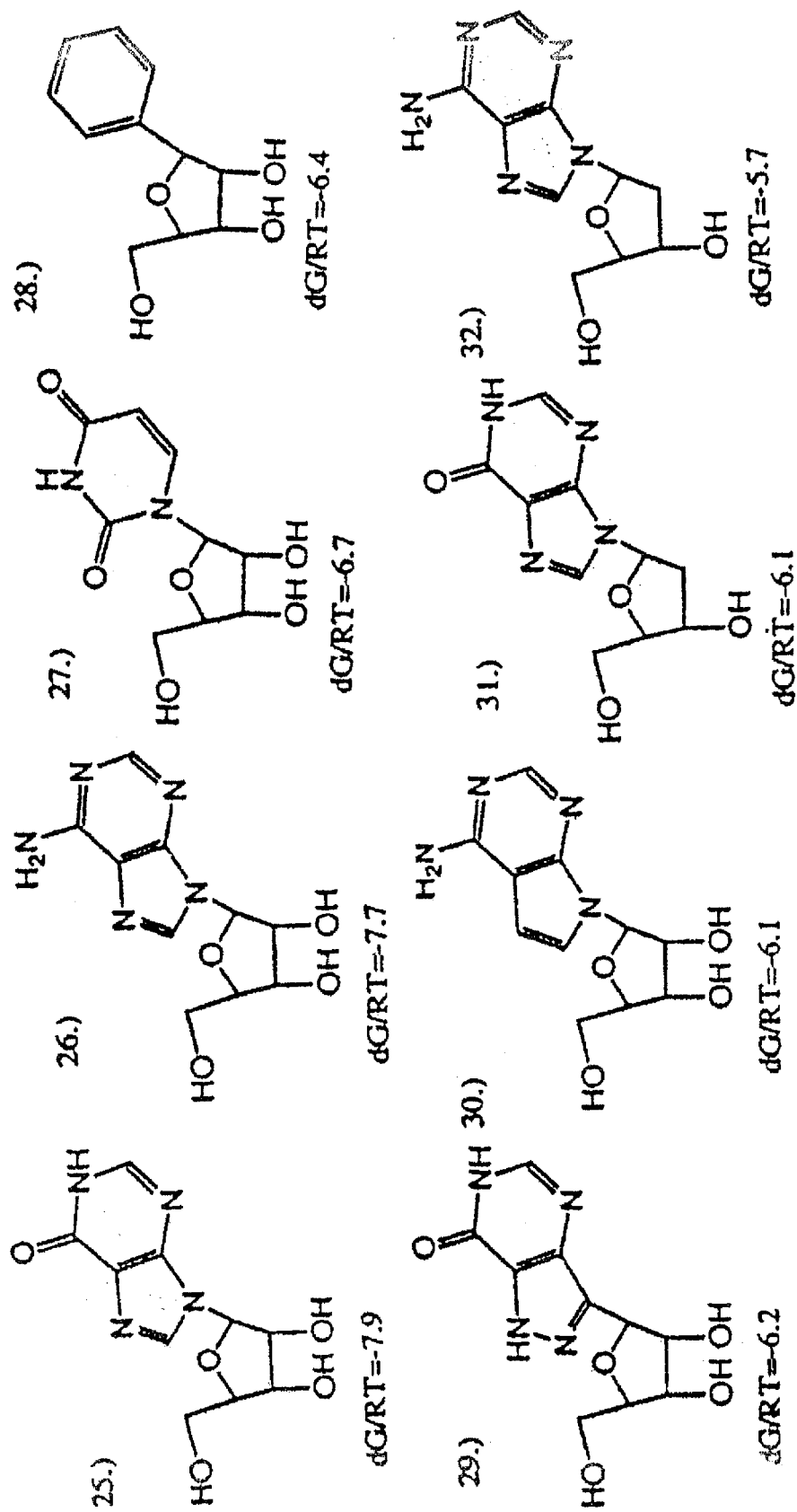

FIGS. 3a–3c, show coincidentally oriented points on the surfaces of some of the molecules used in the study before and after their geometries were modified by the double neural network of the current invention. In FIG. 3a a purine and a pyrimidine analogue are shown oriented for maximum geometric coincidence, the input molecules are numbers 2 and 4 in FIG. 4. As seen in FIGS. 3b and 3c, the optimized versions of the input descriptions of molecules, are compared to their unaltered input descriptions. The neural networks developed herein have the capacity to rearrange the geometry of the inhibitors enough so that if a purine was input into the outer network it could output a pyrimidine to the inner network. In FIGS. 3b and 3c the outer neural network was not found to average the geometric descriptions for the two kinds of inhibitors. This is an important result because from the trends within the molecules of the study that purines bind more tightly as the electron withdrawing tendencies of substituents are increased and the opposite is true for pyrimidines. That is, the enzyme must deal with the two kinds of substrates and inhibitors in different ways, and it is important that the neural network deal with them in different ways as well. It has been determined that the neural network developed herein can learn the different binding rules for the different kinds of inhibitors. The important finding with the double neural network is that it when it is utilized the inner network is able to teach the outer network about the different binding rules as they apply to structurally different molecules. This evidence comes from the fact that purine and pyrimidine geometric characteristics were not averaged.

Idealized Molecules

Figure 5A:
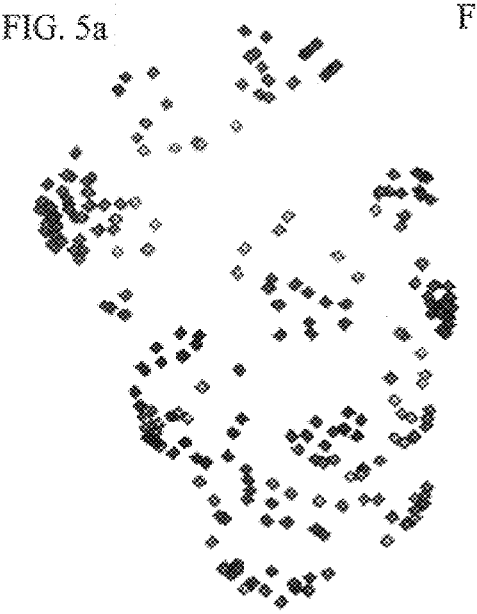
FIGS. 5a and 5c show a surface point comparison of the electrostatic potential of unaltered input molecule number 4, FIG. 5a, with the double neural network idealized form of input molecule 4, FIG. 5c.
Figure 5B:
FIGS. 5b and 5d show a surface point comparison of the geometry of unaltered input molecule number 4, FIG. 5b, with double neural network idealized form of input molecule number 4, FIG. 5d.
Figure 5C:
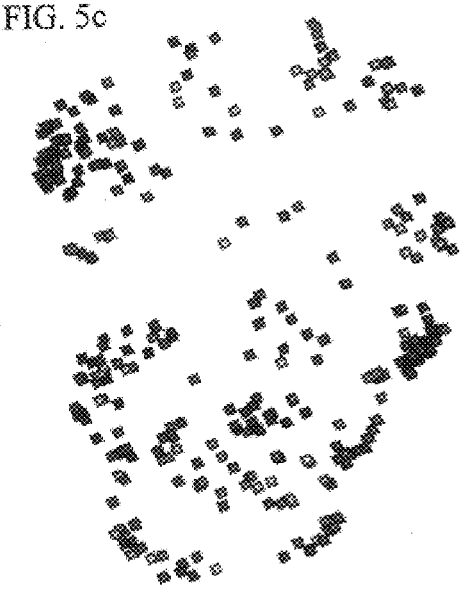
Figure 5D:
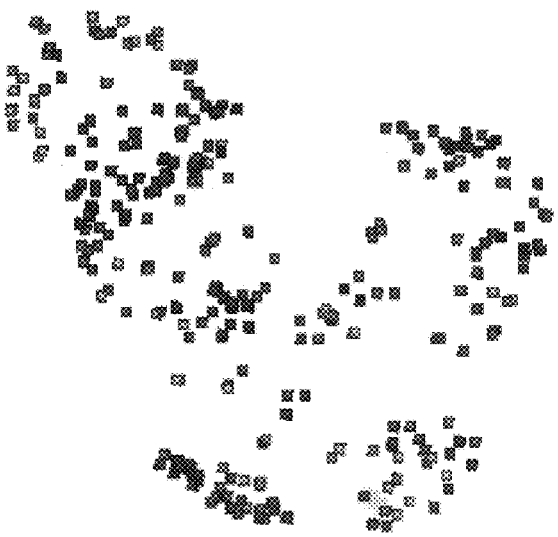
Figure 6A:
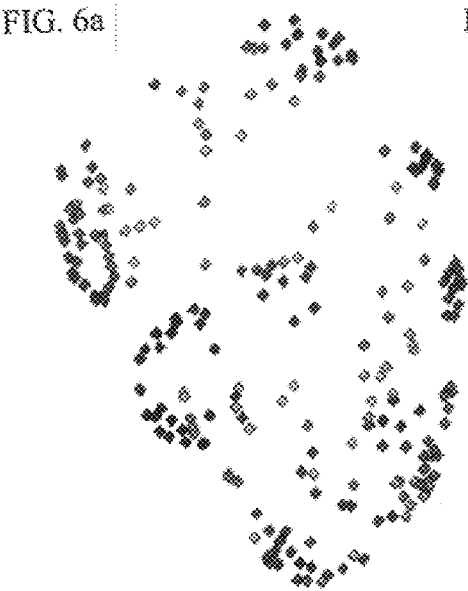
FIGS. 6a and 6c show a surface point comparison of the electrostatic potential of unaltered input molecule number 9, FIG. 6a, with the double neural network idealized form of input molecule number 9, FIG. 6c.
Figure 6B:
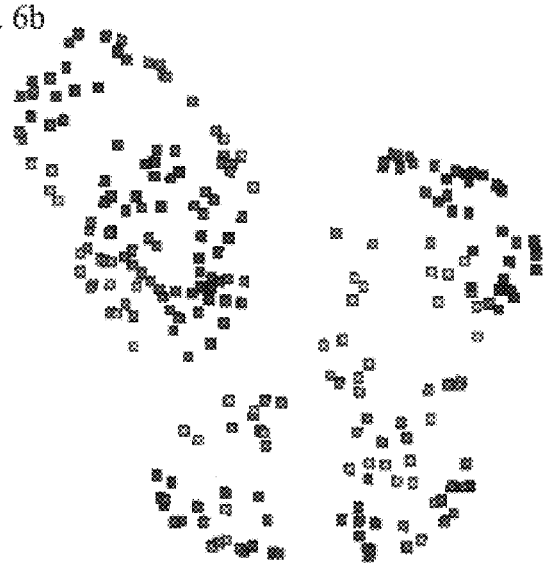
FIGS. 6b and 6d show a surface point comparison of the geometry of the unaltered molecule number 9, FIG. 6b, with the double neural network idealized form of input molecule number 9, FIG. 6d.
Figure 6C:
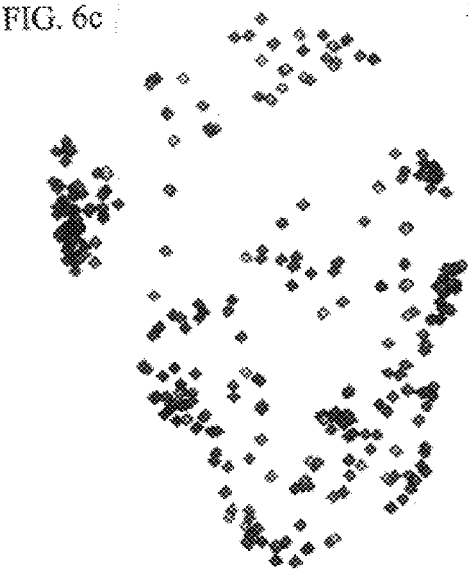
Figure 6D:
Figure 7A:
FIGS. 7a and 7c show a surface point comparison of the electrostatic potential of unaltered input molecule number 14, FIG. 7a, with the double neural network idealized form of molecule number 14, FIG. 7c.
Figure 7B:
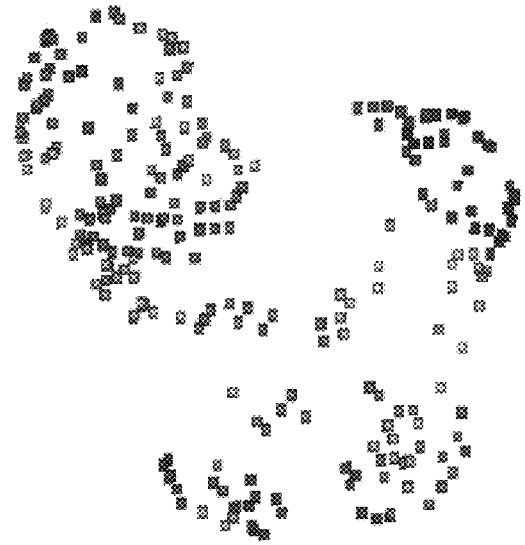
FIGS. 7b and 7d show a surface point comparison of the geometry of unaltered input molecule number 14, FIG. 7b, with the double neural network idealized form of molecule number 14, FIG. 7d.
Figure 7C:
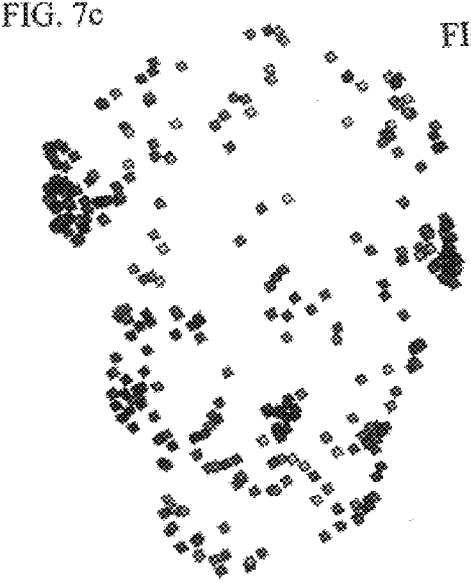
Figure 7D:
Figure 8A:
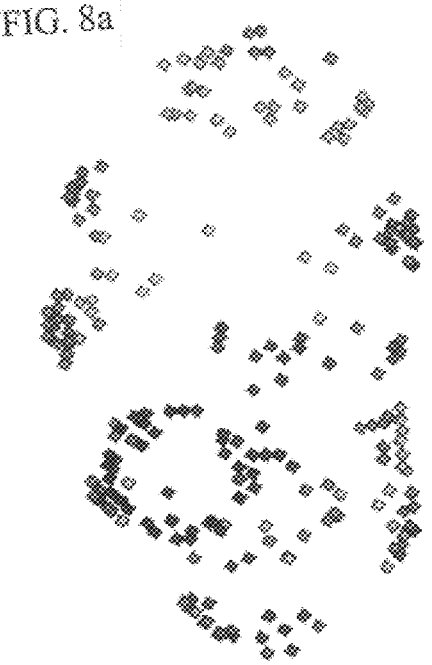
FIGS. 8a and 8c show a surface point comparison of the electrostatic potential of unaltered input molecule number 1, FIG. 8a, with the double neural network idealized form of molecule number 1, FIG. 8c.
Figure 8B:
FIGS. 8b and 8d show a surface point comparison of the geometry of unaltered input molecule number 1, FIG. 8b, with the double neural network idealized form of molecule number 1, FIG. 8d.
Figure 8C:
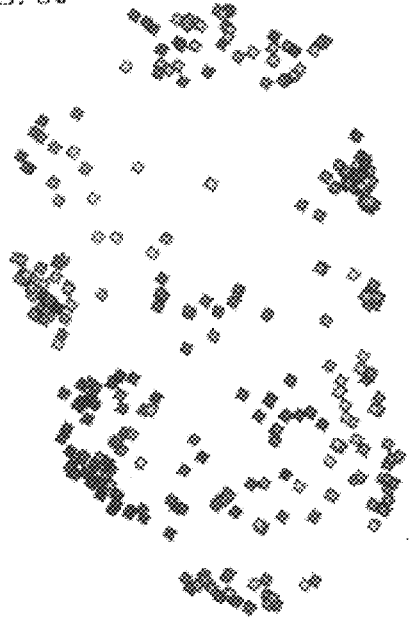
Figure 8D:
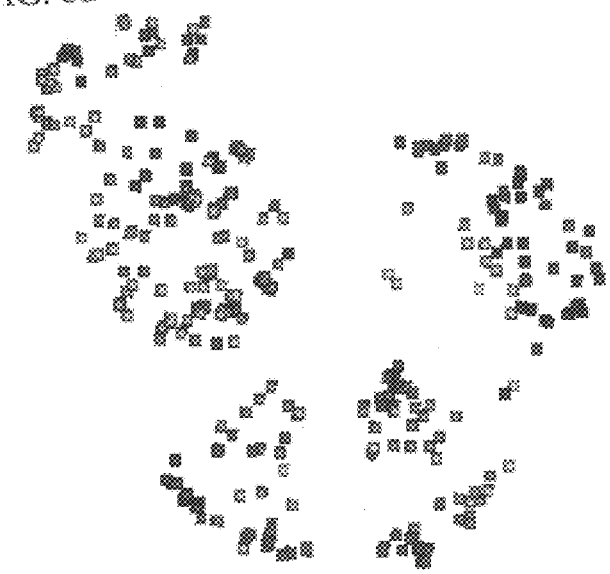
Figure 9A:
FIGS. 9a and 9c show a surface point comparison of the electrostatic potential of unaltered input molecule number 12, FIG. 9a, with the double neural network idealized form of molecule number 12, FIG. 9c.
Figure 9B:
FIGS. 9b and 9d show a surface point comparison of the geometry of unaltered input molecule number 12, FIG. 9b, with the double neural network idealized form of molecule number 12, FIG. 9d.
Figure 9C:
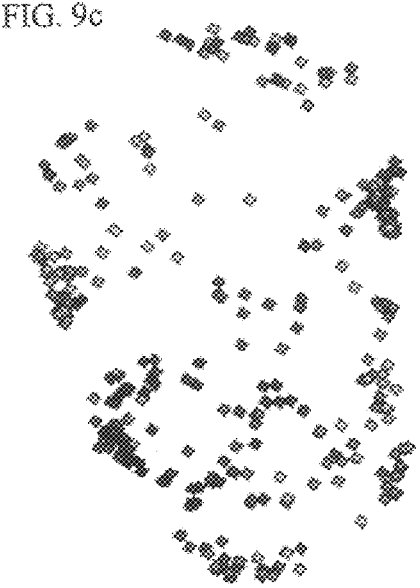
Figure 9D:
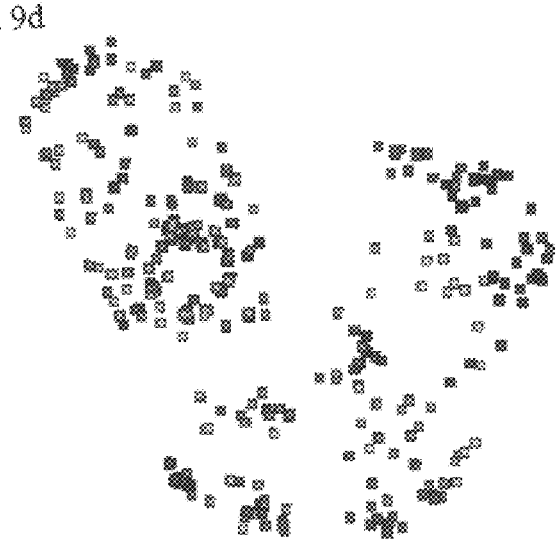
Figure 10A:
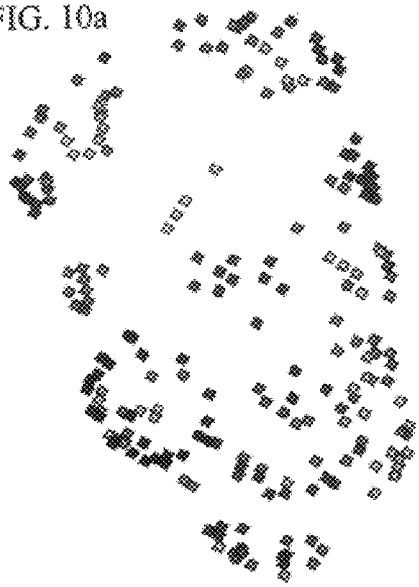
FIGS. 10a and 10c show a surface point comparison of the electrostatic potential of unaltered input molecule number 15, FIG. 10a, with the double neural network idealized form of molecule number 15, FIG. 10c.
Figure 10B:
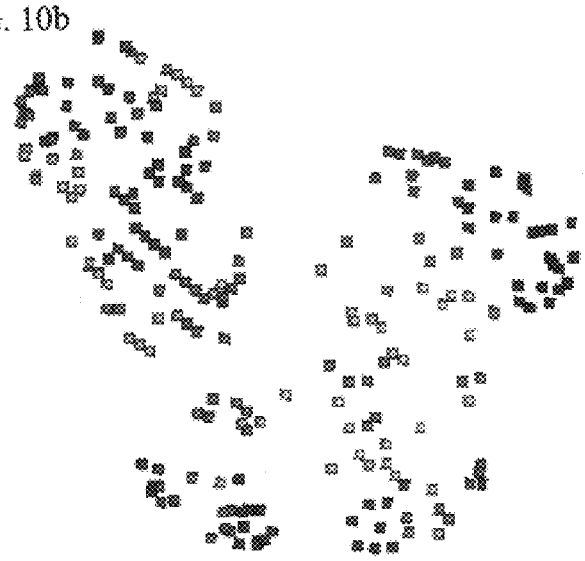
FIGS. 10b and 10d show a surface point comparison of the geometry of unaltered input molecule number 15, FIG. 10b, with the double neural network idealized form of molecule number 15, FIG. 10d.
Figure 10C:
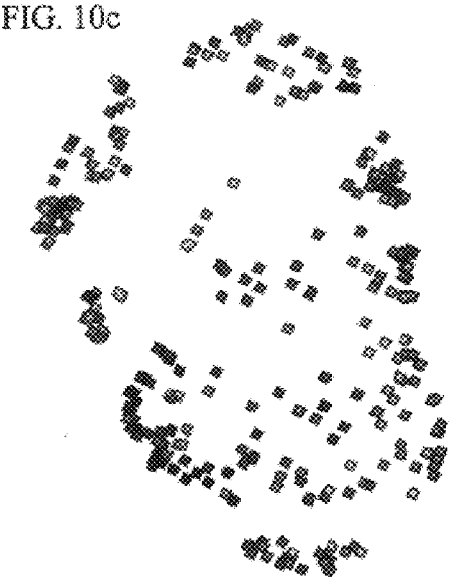
Figure 10D:
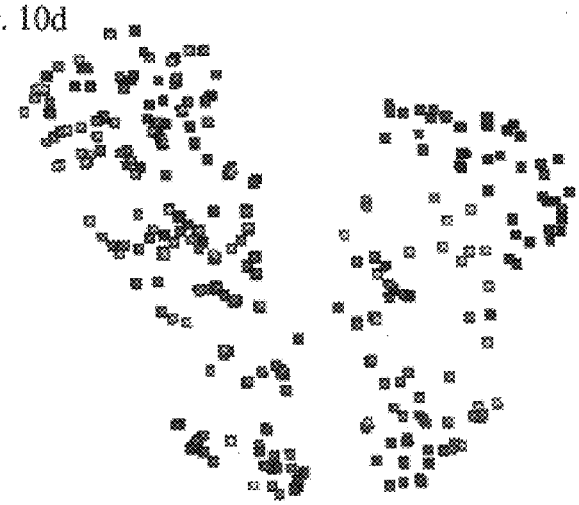

Examination of the idealized molecules, their electrostatic potential and geometry, shows that the double neural network changed purines in different ways than it did for pyrimidines. The purine analogues 4, 9, and 14 were improved by the double neural network in similar ways. The lower right hand side of the surface points shown in FIGS. 5a and 5c show that the neural network improved molecule 4 by making that region more positive. The molecule's entire surface appears to be more positive (red points have a partial positive charge and blue have a partial negative charge), this is consistent with the other improved purines, see FIGS. 6 and 7. This is not surprising, the transition state for inosine is positively charged, it stands to reason that the neural network improve purines by making them look more like the tightest binding purine. In FIG. 7 molecule 14 is shown before and after its description was idealized. Molecule 14 is larger than the other purine analogues, the double neural network improved its description such that it geometrically more resembles the other purines. In order for the double neural network to do this it must have learned that purines analogues that more closely resemble the typical purine form function better. In addition, the double neural network operated on this purine analogue in a different way than it did for any of the other purine analogues. The double neural network of the current invention developed a set of operations that minimized part of the molecule's surface that were applied exclusively to molecule 14.

FIGS. 8 through 10 show that the double neural network idealized pyrimidines by making the lower part of the base more negative. An aromatic ring can be made to be more electron rich by a variety of substituents (Br, OH, $NH_2$) these groups themselves vary greatly in their electrostatic potential, notice how the neural network consistently made the lower portion of the ring more electron rich while the upper part of the ring (where the substituent groups were) is comprised of both positive and negative points. That is, the neural network learned from the molecules in the training set that the top part of the phenyl ring can vary greatly in electrostatic potential, but the electron richness of the mid and lower part of the phenyl ring determines binding strength.

Design of Inhibitors and Chemotherapeutic Compounds

With the effectiveness of the double neural network method provided above, the automation of inhibitor design, rapid drug discovery and/or optimization, and the construction of an apparatus to complete this work becomes possible. The final step of this method is going from the electrostatic potential at the van der Waals surface points to a description of the molecule of interest's atomic coordinates and atom type. This problem involves an increase in complexity going from the input to the output, and is solved by improving the ability of the inner and outer neural network to work together.

Optimizing the Network Function

The inner network was trained within its adjusted co-efficients it contains the rules for binding to the enzyme. Molecular descriptions, in this format can be input to this network and a prediction of binding energy will be output. To show the complexity of the function contained within the trained neural network a random number generator was used to provide output numbers, within the ranges of the molecular descriptions, and see if the function contained within the trained neural network could be optimized randomly. This approach was unsuccessful presumably because there are 400 descriptors in the molecular descriptions used, adjusting them randomly would take an almost infinite amount of time if an exhaustive search is required. Therefore it was determined that a smart search was necessary, that is, the search for every one of the 400 descriptors must be guided toward the optimum value. One problem with this is there is no way to know what the optimum value of the descriptors is until the patterns are presented to the trained neural network and an output is generated and even then, this output will not be able to determine which numbers in the input acted to increase and decrease the output.

Typically, the only place in a neural network where the values of an input are judged for the degree to which they optimize any function is inside the network. The error term and corrections of the hidden layer are:

$$\delta_j = f(h_j^1) \sum_{k=l}^{m} \delta_k w_{jk}$$ Formula [13]

$$\Delta w_{ij} = \alpha \delta_j x_i$$ Formula[14]

$$\Delta b_j = \alpha \delta_j$$ Formula[15]

Equation 13 shows how the error term for the hidden layer, $\delta_j$, is a function of both the input to the hidden layer and the error of the output layer. Equations 14 and 15 show how the error term of the hidden layer is preferably used to calculate the correction terms for the input layer so in the next iteration, the error term will be smaller. This sequence shown in equations 13 through 15 shows how the total error of the network is used to adjust the weights and biases of layers separated from the output layer. The neural network is, in fact, optimizing the input to the hidden layer in spite of the fact that there is no preset optimum of what the hidden layer input should be. This ability of the learning rules to find a multi-dimensional optimum is exactly what is exploited in the double neural network of the current invention.

The "teaching" of the outer network by the inner network occurs because the input layer's error term of the inner network is optimizing the weights and biases of the output layer of the outer network. The reason why quantum features optimization occurs is because the weights and biases of the inner network are fixed and because the true binding energies have been increased slightly. With these configurations the training rules for the double neural network of the current invention were forced to find the multi-dimensional optimum for the output of the outer network's output layer, which is based on minimizing the error of the input layer of the inner network. Preferably, the only way to do this is to output a molecular description that has a slightly larger binding energy than the one input to the outer network. In satisfying these requirements the outer network of the current double neural network becomes a molecular features "optimizer" based on the rules contained within the inner network.

Methods For Generating Input From Quantum Chemical data

A second method can be used to transform the three dimensional surfaces of molecules into a common set of points on a sphere that can then be modeled by the neural networks provided for herein. This transformation works in a similar way as the one layered out above, the first step of this algorithm is to find the angle between the vector defined by line between a point on the sphere and the origin, with the line that connects the origin with every point on the molecular surface. The computer being used is utilized to search through this collection of angles and find five points with the smallest angle. These points are closest to the line that connects the origin and the point of the sphere's surface. From these five points one point that is selected, this point is the one closest to the point of the sphere's surface. Its electrostatic potential is the first number of the input vector. The distance between them is the second number in the input vector.

Five points are used in this method, those with the smallest angle, to find the one point closest to the point of the surface of the sphere (e.g. the smallest distance). The reason for this is that sometimes molecular surfaces are bent or sterically hindered and it is difficult to determine the surface facing away from the center of the molecule. With this method it is possible to determine that the part of the molecular surface with which the molecule of interest interacts is the outermost part of the molecular surface. In this way it is possible to insure that the double neural network of the current invention "sees" the most physically relevant part of the molecule as its input.

Thus, it can be appreciated that a computational method and an apparatus therefore have been presented which will facilitate the discovery of novel bioactive and/or therapeutic molecules, these methods rely on the use of a neural network to recognize and predict binding affinity Accordingly, it is to be understood that the embodiments of the invention herein providing for a more efficient mode of drug discovery and modification are merely illustrative of the application of the principles of the invention. It will be evident from the foregoing description that changes in the form, methods of use, and applications of the elements of the neural network system and associated algorithms disclosed may be resorted to without departing from the spirit of the invention, or the scope of the appended claims.

What is claimed is:

1. A computerized neural network system for predicting the chemical activity of at least one molecule of interest comprising:
    a) an input layer consisting of at least one neuron where input data is sent as a vector value;
    b) a weight matrix where every entry in the form of an input vector is multiplied by a set weight and then sent to at least one hidden layer neuron;
    c) a hidden layer consisting of at least one neuron such that when said input vector is multiplied by a set weight said hidden layer contains said weight matrix, said weight matrix having the dimensions n by m where n is the length of an input vector and m is the number of hidden layer neurons available;
    d) an output layer consisting of at least one neuron where weight matrix data is sent before it is input into a transfer function;
    e) a transfer function that is non-linear in form and is capable of taking any value generated by said output layer and returning a number between −1 and 1 or another predetermined range;
    f) a training process for said neural network such that said neural network can accurately approximate a free energy of binding of at least one known training molecule with an output from said output layer; and
    g) a test process in which a trained neural network is used to predict a free energy of binding for said at least one molecule of interest;
        wherein the physicochemical descriptor of said at least one molecule of interest is the quantum mechanical electrostatic potential of said at least one molecule of interest at the van der Waals surface of said at least one molecule of interest and, wherein said test process Includes the use of at least one adjuster molecule such that after said training process said neural network is used to predict a free energy of binding for said at least one adjuster molecule, said at least one adjuster molecule having a known free energy of binding and having been excluded from the set of molecules comprising the set of said of at least one known training molecule.

2. The neural network of claim 1, wherein said neural network is able to accurately predict the free energy of binding of said at least one adjuster molecule within 10%.

3. A computerized double neural network system for predicting the chemical activity of at least one molecule of interest comprising:

a) an outer neural network further comprising:
    i) an outer network input layer consisting of at least one neuron where input data is sent as a vector value;
    ii) an outer network weight matrix where every entry in the form of an input vector is multiplied by a set weight and then sent to at least one hidden layer neuron;
    iii) an outer network hidden layer consisting of at least one neuron such that when said input vector Is multiplied by a set weight said hidden layer contains said weight matrix, said weight matrix having the dimensions n by m where n is the length of an input vector and m is the number of hidden layer neurons available;
    iv) an outer network output layer consisting of at least one neuron where weight matrix data is sent before it is input into a transfer function;
    v) an outer network transfer function that is non-linear in form and is capable of taking any value generated by said output layer and returning a number between −1 and 1 or another predetermined range;
    vi) a training process for said outer neural network such that said neural network can accurately approximate a free energy of binding of at least one known training molecule with an output from said output layer;
b) an inner neural network capable of receiving data from said outer neural network further comprising:
    i) an inner network weight matrix where every entry in the form of an input vector is multiplied by a set weight and then sent to at least one hidden layer neuron;
    ii) an inner network hidden layer consisting of at least one neuron such that when said input vector is multiplied by a set weight said hidden layer contains said weight matrix, said weight matrix having the dimensions n by m where n is the length of an input vector and m is the number of hidden layer neurons available;
    iii) an inner network output layer consisting of at least one neuron where weight matrix data is sent before it is input into a transfer function said inner network output layer having an output value;
    iv) an inner network transfer function that is non-linear in form and is capable of taking said output value generated by said output layer and returning a number between −1 and 1 or another predetermined range;
    v) a training process for said inner neural network such that said neural network can accurately approximate a free energy of binding of at least one known training molecule with an output from said output layer
    vi) a test process in which a trained neural network is used to predict a free energy of binding for said at least one molecule of interest;
        wherein said inner neural network is integrated to function with the data generated from said outer neural network such that the rules for said free energy of binding learned by said outer neural network are utilized by said inner neural network to model a quantum object such that said double neural network is used to predict the chemical characteristics of said quantum object, said quantum object describing a molecule with improved chemical properties of binding relative to said at least one molecule of interest;

wherein said outer network output layer is the input layer of said inner neural network;

wherein said outer network hidden layer includes an error term, said error term being used to calculate the correction terms for said outer network input layer such that the weights and biases of said double neural network are optimized; and wherein the physicochemical descriptor of said at least one molecule of interest is the quantum mechanical electrostatic potential of said at least one molecule of interest at the van der Waals surface of said at least one molecule of interest.

4. The double neural network of claim 3, wherein said test process includes the use of at least one adjuster molecule such that after said outer network training process said neural network is used to predict a free energy of binding for said at least one adjuster molecule, said at least one adjuster molecule having a known free energy of binding and having been excluded from the set of molecules comprising the set of said of at least one known training molecule.

5. The double neural network of claim 4, wherein said double neural network is able to accurately predict the free energy of binding of said at least one adjuster molecule within 10%.

6. The double neural network of claim 3, wherein only the weights and biases of said outer network weight matrix are allowed to vary during the training of said double neural network.

7. The double neural network of claim 3, wherein a bias is added to said outer network hidden layer and said outer network output layer neurons such that all values are scaled before they are input into said outer network transfer function.

8. The double neural network of claim 3, wherein said outer network hidden layer is composed of 5 hidden layer neurons.

9. The double neural network of claim 3, wherein said inner network hidden layer is composed of 5 hidden layer neurons.

10. The double neural network of claim 3, wherein said double neural network is run through at least 100,000 iterations.

11. The double neural network of claim 3, wherein the learning rate of said outer neural network is 0.1.

12. The double neural network of claim 3, wherein the learning rate of said inner neural network is 0.1.

13. The double neural network of claim 3, wherein the momentum term of said outer neural network is 0.9.

14. The double neural network of claim 3, wherein the momentum term of said inner neural network is 0.9.

15. The double neural network of claim 3, wherein the quantum chemical data sent to said outer network input layer is a vector value derived from calculating the electrostatic potential of a molecule at the van der Waals surface.

16. The double neural network of claim 15, wherein said computer is coupled to a display device and there exists a means for presenting the chemical properties of said at least one molecule of interest on said display device.

17. The double neural network of claim 3, wherein the process for carrying out the elements of said double neural network for predicting the chemical activity of said at least one molecule of interest are contained in a computer, said computer being capable of receiving data and performing said training process and said testing process.

18. The double neural network of claim 17, wherein the chemical characteristics of said quantum object are in the form of a three dimensional representation, said three dimensional representation allowing the identification of the molecular features of said quantum object that said double neural network determined could altered to improve the chemical characteristics of said at least one molecule of interest.

19. The double neural network of claim 3, wherein said at least one molecule of interest is selected from the group consisting of:

a) a pharmaceutical;
b) an enzyme;
c) a catalyst;
d) a polypeptide;
e) an amino acid derivative;
f) a carbohydrate;
g) a nucleotide;
h) a macromolecular compound;
i) an organic moiety of an alkyl, cycloalkyl, aryl, aralkyl or alkaryl group or a substituted or heterocyclic derivative thereof;
j) an industrial compound; and
k) a polymer.

20. The double neural network of claim 19, wherein said at least one molecule of interest is an enzyme.

21. The method of claim 20, wherein said at least one molecule of interest is selected from the group consisting of:

a) a pharmaceutical;
b) an enzyme;
c) a catalyst;
d) a polypeptide;
e) an amino acid derivative;
f) a carbohydrate;
g) a nucleotide;
h) a macromolecular compound;
i) an organic moiety of an alkyl, cycloalkyl, aryl, aralkyl or alkaryl group or a substituted or heterocyclic derivative thereof; and
j) an industrial compound; and
k) a polymer.

22. The double neural network of claim 3, wherein said output value is decreased by at least $1\Delta G/RT$.

23. The double neural network of claim 3, wherein said output value is decreased by $3\Delta G/RT$.

24. A computer implemented method for predicting the chemical activity of at least one molecule of interest by using a neural network comprising:

a) inputting data into an input layer consisting of at least one neuron where input data is sent as a vector value;

b) developing a weight matrix wherein every entry in the form of an input vector is multiplied by a set weight and then sent to at least one hidden layer neuron;

c) providing a hidden layer consisting of at least one neuron such that when said input vector is multiplied by a set weight said hidden layer contains said weight matrix, said weight matrix having the dimensions n by m where n is the length of an input vector and m is the number of hidden layer neurons available;

d) constructing an output layer consisting of at least one neuron where weight matrix data is sent before it is input into a transfer function;

e) utilizing a transfer function that is non-linear in form and is capable of taking any value generated by said output layer and returning a number between −1 and 1;

f) employing a training process for said neural network such that said neural network can accurately approximate a free energy of binding of at least one known training molecule with an output from said output layer; and employing a test process in which a trained neural network is used to predict a free energy of binding for said at least one molecule of interest wherein the physicochemical descriptor of said at least one molecule of interest is the quantum mechanical electrostatic potential of said at least one molecule of interest at the van der Waals surface of said at least one molecule of interest, wherein said test process includes the use of at least one adjuster molecule such that after said training process said neural network is used to predict a free energy of binding for said at least one adjuster molecule, said at least one adjuster molecule having a known free energy of binding and having been excluded from the set of molecules comprising the set of said of at least one known training molecule.

25. The method of claim 24, wherein said neural network is able to accurately predict the free energy of binding of said at least one adjuster molecule within 10%.

26. A computer implemented method for predicting the chemical activity of at least one molecule of interest by using a double neural network comprising:
   a) utilizing an outer neural network further comprising:
      i) an outer network input layer consisting of at least one neuron where input data is sent as a vector value;
      ii) an outer network weight matrix where every entry in the form of an input vector is multiplied by a set weight and then sent to at least one hidden layer neuron;
      iii) an outer network hidden layer consisting of at least one neuron such that when said input vector is multiplied by a set weight said hidden layer contains said weight matrix, said weight matrix having the dimensions n by m where n is the length of an input vector and m is the number of hidden layer neurons available;
      iv) an outer network output layer consisting of at least one neuron where weight matrix data is sent before it is input into a transfer function;
      v) an outer network transfer function that is non-linear in form and is capable of
   b) taking any value generated by said output layer and returning a number between −1 and 1;
      i) an outer network training process for said neural network such that said neural network can accurately approximate a free energy of binding of at least one known training molecule with an output from said output layer;
   c) providing an inner neural network capable of receiving data from said outer neural network further comprising:
      i) an inner network weight matrix where every entry in the form of an input vector is multiplied by a set weight and then sent to at least one hidden layer neuron;
      ii) an inner network hidden layer consisting of at least one neuron such that when said input vector is multiplied by a set weight said hidden layer contains said weight matrix, said weight matrix having the dimensions n by m where n is the length of an input vector and m is the number of hidden layer neurons available;
      iii) an inner network output layer consisting of at least one neuron where weight matrix data is sent before it is input into a transfer function said inner network output layer having an output value;
      iv) an inner network transfer function that is non-linear in form and is capable of taking any value generated by said output layer and returning a number between −1 and 1;
      v) an inner network training process for said neural network such that said neural network can accurately approximate a free energy of binding of at least one known training molecule with an output from said output layer;
      vi) a test process in which a trained neural network is used to predict a free energy of binding for said at least one molecule of interest:
   d) integrating said inner neural network to function with the data generated from said outer neural network such that the rules for said free energy of binding learned by said outer neural network are utilized by said inner neural network to model a quantum object such that said double neural network is used to predict the chemical characteristics of said quantum object, said quantum object describing a molecule with improved chemical properties of binding relative to said at least one molecule of interest;
   e) constructing said outer network input layer such that said output layer of said outer neural network is the input layer of said inner neural network; and
   f) providing said outer network hidden layer with an error term, said error term being used to calculate the correction terms for said outer network input layer such that the weights and biases of said double neural network are optimized;
   wherein the physicochemical descriptor of said at least one molecule of interest is the quantum mechanical electrostatic potential of said at least one molecule of interest at the van der Waals surface of said at least one molecule of interest.

27. The double neural network of claim 26, wherein said test process includes the use of at least one adjuster molecule such that after said outer network training process said neural network is used to predict a free energy of binding for said at least one adjuster molecule, said at least one adjuster molecule having a known free energy of binding and having been excluded from the set of molecules comprising the set of said of at least one known training molecule.

28. The double neural network of claim 27, wherein said double neural network is able to accurately predict the free energy of binding of said at least one adjuster molecule within 10%.

29. The double neural network of claim 26, wherein only the weights and biases of said outer network weight matrix are allowed to vary during the training of said double neural network.

30. The double neural network of claim 26, wherein a bias is added to said outer network hidden layer and said outer network output layer neurons such that all values are scaled before they are input into said outer network transfer function.

31. The double neural network of claim 26, wherein said outer network hidden layer is composed of 5 hidden layer neurons.

32. The double neural network of claim 26, wherein said inner network hidden layer is composed of 5 hidden layer neurons.

33. The double neural network of claim 26, wherein said double neural network is run through at least 100,000 iterations.

34. The double neural network of claim 26, wherein the learning rate of said outer neural network is 0.1.

35. The double neural network of claim 26, wherein the learning rate of said inner neural network is 0.1.

36. The double neural network of claim 26, wherein the momentum term of said outer neural network is 0.9.

37. The double neural network of claim 26, wherein the momentum term of said inner neural network is 0.9.

38. The double neural network of claim 37, wherein said computer is coupled to a display device and there exists a means for presenting the chemical properties of said at least one molecule of interest on said display device.

39. The double neural network of claim 26, wherein the quantum chemical data sent to said outer network input layer is a vector value derived from calculating the electrostatic potential of a molecule at the van der Waals surface.

40. The double neural network of claim 26, wherein the process for carrying out the elements of said double neural network for predicting the chemical activity of said at least one molecule of interest are contained in a computer, said computer being capable of receiving data and performing said training process and said testing process.

41. The double neural network of claim 26, wherein said at least one molecule of interest is selected from the group consisting of:
a) a pharmaceutical;
b) an enzyme;
c) a catalyst;
d) a polypeptide;
e) an amino acid derivative;
f) a carbohydrate;
g) a nucleotide;
h) a macromolecular compound;
i) an organic moiety of an alkyl, cycloalkyl, aryl, aralkyl or alkaryl group or a substituted or heterocyclic derivative thereof;
j) an industrial compound; and
k) a polymer.

42. The double neural network of claim 26, wherein said output value is decreased by at least $1\Delta G/RT$.

43. The double neural network of claim 26, wherein said output value is decreased by $3\Delta G/RT$.

44. A computerized neural network system comprising a neural network having a first component trained to recognize binding energy for a first set of molecular descriptors based on geometric and/or electrostatic information and for a given binding energy returning a second set of the molecular descriptors through a second component of the network.

45. A computerized double neural network system comprising a trained neural network for predicting binding potency for a chemotherapeutic agent with a target molecule, the network having an input layer, and the network being coupled to an output layer of an outer neural network comprising one or more layers so that the output of the output layer of the outer neural network is the input to the input layer of the inner neural network.

46. The system of claim 45 wherein the chemotherapeutic agent is an inhibitor and the molecule is an enzyme.

47. A computer implemented method comprising providing a neural network having a first component trained to recognize binding energy for a first set of molecular descriptors based on geometric and/or electrostatic information and for a given binding energy returning a second set of the molecular descriptors through a second component of the network.

48. A computer implemented method comprising providing a trained neural network for predicting binding potency for a chemotherapeutic agent with a target molecule, the network having an input layer, coupling the network to an output layer of an outer neural network comprising one or more layers so that the output of the output layer of the outer neural network is the input to the input layer of the inner neural network.

49. A computer implemented method comprising providing a trained neural network for predicting binding potency for a chemotherapeutic agent with a target molecule, the network having an input layer coupled to an output layer of an outer neural network comprising one or more layers so that the output of the output layer of the outer neural network is the input to the input layer of the inner neural network, and inputting molecular descriptors based on geometric and/or electrostatic information into the input layer from the coupled outer layer.

50. The method of claim 48 wherein the chemotherapeutic agent is an inhibitor and the molecule is an enzyme.

51. A computer implemented method of customizing the binding features of a molecule of interest comprising:
providing a neural network comprising a first component trained to recognize binding energy for first set of molecular descriptors based on electrostatic and/or geometrical information, and for a given binding energy returning a second set of the molecular descriptors through a second component of the network;
selecting a molecule of interest and modifying it so that the resulting molecule has a set of molecular descriptors that more closely matches descriptors in the second set of descriptors returned by the second component of the network.

52. A computer implemented method of determining a set of molecular descriptors:
providing a neural network comprising an inner network trained to predict binding energy of a molecule of interest with a target molecule using a set of molecular descriptors based on geometric and/or electrostatic information for the molecule of interest the inner network having an input layer coupled to the output layer of an outer neural network for inputting molecular descriptors,
in the inner neural network, setting the binding energy for an unknown molecule of interest to a desired level; and
determining a set of molecular descriptors for an unknown molecule of interest by computing through the network a set of molecular descriptors that if output from the output layer of the outer neural network would yield a binding energy within a desired range of a predetermined binding energy set for the inner neural network.

53. The method of claim 52 wherein the target molecule comprises a protein having a binding site and the molecular descriptors are for an unknown target molecule that is a potential binding agent of the binding site and wherein the binding energy is set at least slightly above the binding energy of a known binding agent for the binding site.

54. The method of claim 53 wherein the protein is an enzyme and the binding agent is an inhibitor.

55. The method of claim 52 wherein there is a total of 5 inner and outer network layers.

56. The method of claim 52 wherein the molecular descriptors comprise electrostatic potential and geometric information.

57. The method of claim 52 wherein the binding energy level is set to a desired degree higher than the binding energy for a known molecule of interest and wherein the method further comprises determining the chemical structure of a molecule using the molecular descriptors for the unknown molecule of interest.

58. The method of claim 57 wherein the determined structure is derived from optimizing binding features in a known molecule of interest.

59. The method of claim 57 wherein the determined structure is a modification of a known molecule of interest having a known binding energy with the target molecule.

* * * * *